United States Patent
Adams et al.

(10) Patent No.: US 11,623,902 B2
(45) Date of Patent: *Apr. 11, 2023

(54) SELECTIVE HYDROGENATION METHODS AND CATALYSTS

(71) Applicant: Clariant International Ltd, Muttenz (CH)

(72) Inventors: Darren Adams, The Woodlands, TX (US); Mingyong Sun, Louisville, KY (US); Uwe Duerr, Germering (DE); Denise Cooper, Houston, TX (US); Brian Heasley, Houston, TX (US); Ling Xu, Munich (DE); Tina Clinton, Louisville, KY (US)

(73) Assignee: Clariant International Ltd, Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/660,119

(22) Filed: Oct. 22, 2019

(65) Prior Publication Data

US 2020/0123083 A1    Apr. 23, 2020

Related U.S. Application Data

(60) Provisional application No. 62/749,456, filed on Oct. 23, 2018.

(51) Int. Cl.
| | |
|---|---|
| *C07C 5/09* | (2006.01) |
| *B01J 31/02* | (2006.01) |
| *B01J 31/28* | (2006.01) |
| *B01J 21/04* | (2006.01) |
| *B01J 23/44* | (2006.01) |
| *B01J 35/10* | (2006.01) |
| *B01J 37/02* | (2006.01) |
| *B01J 37/08* | (2006.01) |
| *B01J 23/50* | (2006.01) |

(52) U.S. Cl.
CPC .............. *C07C 5/09* (2013.01); *B01J 21/04* (2013.01); *B01J 23/44* (2013.01); *B01J 23/50* (2013.01); *B01J 31/0277* (2013.01); *B01J 31/28* (2013.01); *B01J 35/1009* (2013.01); *B01J 35/1014* (2013.01); *B01J 35/1038* (2013.01); *B01J 37/0203* (2013.01); *B01J 37/024* (2013.01); *B01J 37/0205* (2013.01); *B01J 37/0236* (2013.01); *B01J 37/08* (2013.01); *B01J 37/088* (2013.01); *C07C 2521/04* (2013.01); *C07C 2523/44* (2013.01); *C07C 2523/50* (2013.01)

(58) Field of Classification Search
CPC ... C07C 5/09; C07C 2521/04; C07C 2523/44; C07C 2523/50; C07C 7/167; C07C 2531/02; C07C 2531/025; B01J 23/44; B01J 23/50; B01J 31/0277; B01J 31/0279; B01J 31/0284; B01J 31/0288; B01J 31/28; B01J 35/008; B01J 35/023; B01J 35/026; B01J 35/1009; B01J 35/1014; B01J 35/1038; B01J 37/0201; B01J 37/0203; B01J 37/0205; B01J 37/0236; B01J 37/08; B01J 37/088; B01J 21/04; B01J 2231/645; Y02P 20/52

See application file for complete search history.

(56) References Cited

U.S. PATENT DOCUMENTS

| | | | |
|---|---|---|---|
| 4,126,645 A | 11/1978 | Collins | |
| 6,576,588 B2 * | 6/2003 | Ryu | ........................ C07C 7/167 502/331 |
| 2005/0113613 A1 * | 5/2005 | Molinier | ................ B01J 23/896 585/258 |
| 2013/0102819 A1 | 4/2013 | Szesni | |
| 2016/0214913 A1 * | 7/2016 | Nawaz | ...................... C07C 5/09 |

FOREIGN PATENT DOCUMENTS

EP    2583751    4/2013

OTHER PUBLICATIONS

Zhou Ting et al, "Ionic liquid and plasma effects on SiO2supported Pd for selective hydrogenation of acetylene", Catalysis Today, Elsevier, Amsterdam, NL, vol. 211, Mar. 29, 2013 (Mar. 29, 2013), p. 147-155.

Xu Yiqi et al, "Highly selectivity catalytic hydrogenation of acetylene on Al2O3supported palladium-imidazolium based ionic liquid phase", Applied Catalysis A: General, Elsevier, Amsterdam, NL,vol. 567, Sep. 9, 2018 (Sep. 9, 2018), p. 12-19.

Michael F. Friedrich et al, "Selective hydrogenation of propyne on a solid Pd/Al 2 O 3 catalyst modified with ionic liquid layer (SCILL)", Catalysis Communications,vol. 88, Jan. 1, 2017 (Jan. 1, 2017), p. 73-76.

* cited by examiner

*Primary Examiner* — In Suk C Bullock
*Assistant Examiner* — Jason Y Chong

(57) ABSTRACT

The present disclosure relates to methods for selectively hydrogenating acetylene, to methods for starting up a selective hydrogenation reactor, and to hydrogenation catalysts useful in such methods. In one aspect, the disclosure provides a method for selectively hydrogenating acetylene, the method comprising contacting a catalyst composition with a process gas. The catalyst composition comprises a porous support, palladium, and one or more ionic liquids. The process gas includes ethylene, present in the process gas in an amount of at least 20 mol. %; and acetylene, present in the process gas in an amount of at least 1 ppm. At least 90% of the acetylene present in the process gas is hydrogenated, and the selective hydrogenation is conducted without thermal runaway. Notably, the process gas is contacted with the catalyst at a gas hourly space velocity (GHSV) based on total catalyst volume in one bed or multiple beds of at least 7,100 $h^{-1}$.

22 Claims, 7 Drawing Sheets

SELECTIVE HYDROGENATION METHODS AND CATALYSTS

CROSS-REFERENCE TO RELATED APPLICATIONS

This application claims the benefit of priority of U.S. Provisional Patent Application No. 62/749,456, filed Oct. 23, 2018, which is hereby incorporated herein by reference in its entirety.

BACKGROUND OF THE DISCLOSURE

Field of the Disclosure

The disclosure relates generally to hydrogenation methods and to hydrogenation catalysts. More particularly, the present disclosure relates to methods for selectively hydrogenating acetylene, for example, in front end processes; to methods for starting up a selective hydrogenation reactor, for example, in front end processes; and to hydrogenation catalysts useful in such methods.

Technical Background

Olefins are important monomers for the production of plastics. For example, ethylene and propylene are polymerized to form polyethylene and polypropylene, respectively. Olefins such as ethylene and propylene are typically derived from petroleum products through thermal or catalytic cracking of hydrocarbons. However, cracking provides a crude olefin mixture that can contain acetylene, which can interfere with the downstream polymerization of ethylene and propylene. It can be desirable to "clean up" this process gas to selectively convert acetylene to ethylene without substantial reduction of any olefins present or the acetylene itself to alkanes.

There are two main reactor configurations for selective hydrogenation of acetylene in ethylene-rich streams—so-called tail-end (or back end) processes, and front end processes. In the tail-end configuration, the selective hydrogenation reactor feed typically consists mainly of C2 hydrocarbons, and stoichiometric amounts of hydrogen with respect to acetylene are added to this feed gas stream to ensure an optimal concentration of hydrogen (typically 1%-4% mol. %) in the feed stream to the reactor. Carbon monoxide is typically not present in the feed stream in amounts greater than 2 ppm; in some conventional processes, CO is separately added to the reactor inlet stream. In the front-end configuration, the selective hydrogenation reactor feed typically contains a large excess of hydrogen, e.g., 10-35 mol % of hydrogen, together with carbon monoxide, acetylenes, olefins and other hydrocarbons. In a front-end deethanizer design, the reactor feed contains a C2 and lighter stream, while in front-end depropanizer unit, the reactor feed contains C3 and lighter hydrocarbons. Carbon monoxide is generally present in such feed streams, in concentrations varying from below 100 ppm to 3000 ppm.

Conventionally, front end selective hydrogenation of acetylene present in an olefin rich mixture is performed by using optionally-promoted palladium-shell catalysts. However, the activity of the hydrogenation catalyst under the process conditions must be carefully limited to avoid thermal runaway (an uncontrolled feedback loop, in which heat from the exothermic hydrogenation reaction increases the catalyst temperature, in turn increasing the rate of the hydrogenation reaction, which provides even more heat, etc.), which can result in an undesirable overreduction of ethylene to ethane and even in shutdown of reactor due to an uncontrollable temperature rise in the reactor. Conventional front end selective hydrogenation processes are so limited through strict control of the temperature, which is kept below a certain temperature (e.g., a runaway temperature). Conventional front end selective hydrogenation processes are limited by gas hourly space velocity (GHSV), so that the temperature due to the exothermic hydrogenation reaction required to clean-up acetylene does not rise too high, so as not to approach a temperature that may result in thermal runaway.

Moreover, reactors for such conventional front end selective hydrogenation processes, particularly those containing fresh catalyst, must be started up particularly carefully to avoid thermal runaway. Conventionally, it was understood that the initial contact of the catalyst bed with process gas (i.e., containing hydrogen, olefin and acetylene) flow must be made at low temperature to avoid runaway. But at such low temperatures, reduction of acetylene is typically not complete and so the acetylene concentration in the reactor effluent is higher than the product specification allows. While process gas flows, the catalyst bed temperature is then raised very slowly to a desired reaction temperature at which the acetylene concentration meets specification. The temperature rise is often on the order of a degree Celsius per hour, and so the start-up procedure can take over twenty hours to provide on-specification output. During the start-up period, the out-of-specification effluent from the reactor is often sent to flare.

In addition to strict temperature control, conventionally, during start-up the reactor is pre-charged with CO and pressurized with non-reactive gases before the catalyst is heated. The composition of the reactor gas mixture is slowly shifted towards the process gas (i.e., containing hydrogen, acetylene and one or more olefins). This startup process not only has safety concerns due to the use of a large quantity of CO gas on site, but it is also costly, due to material costs, to lost production time, and to treatment/disposal of the reactor output before the reactor is fully operational.

Accordingly, there remains a need for a method for selectively hydrogenating acetylene at high throughput, and/or at a low concentration of CO, but without undue risk of thermal runaway. There also remains a need for a method for starting up a hydrogenation reactor that does not require pre-charge of the reactor with CO, nor inert gas pressurization, and/or that can be conducted in a short period of time.

SUMMARY OF THE DISCLOSURE

The present inventors have discovered that the catalysts described herein have especially advantageous properties that allow for new methods of selective hydrogenation of acetylene.

Accordingly, one aspect of the disclosure is a method for selectively hydrogenating acetylene, the method comprising contacting a catalyst composition comprising a porous support, palladium, and at least one ionic liquid with a process gas comprising ethylene, present in the process gas in an amount of at least 10 mol. %;
  acetylene, present in the process gas in an amount of at least 1 ppm;
  hydrogen, present in the process gas in amount of at least 5 mol. %; and
  0 ppm to 190 ppm carbon monoxide;

wherein at least 90% of the acetylene present in the process gas is hydrogenated, and no more than 1 mol. % of the total of acetylene and ethylene present in the process gas is converted to ethane.

Another aspect of the disclosure is a method for selectively hydrogenating acetylene, the method comprising contacting a catalyst composition comprising a porous support, palladium, and at least one ionic liquid with a process gas comprising ethylene, present in the process gas in an amount of at least 10 mol. %;
acetylene, present in the process gas in an amount of at least 1 ppm;
hydrogen, present in the process gas in amount of at least 5 mol. %; and
at least 600 ppm carbon monoxide;
wherein at least 90% of the acetylene present in the process gas is hydrogenated, and no more than 1 mol. % of the total of acetylene and ethylene present in the process gas is converted to ethane.

Another aspect of the disclosure is method for selectively hydrogenating acetylene, the method comprising contacting a catalyst composition comprising a porous support, palladium, and at least one ionic liquid with a process gas comprising
ethylene, present in the process gas in an amount of at least 10 mol. %;
acetylene, present in the process gas in an amount of at least 1 ppm;
hydrogen, present in the process gas in amount of at least 5 mol. %; and
wherein the process gas is contacted with the catalyst at an overall gas hourly space velocity (GHSV) of at least 7,100 h$^{-1}$ (e.g., 7,500 h$^{-1}$ to 40,000 h$^{-1}$) based on total catalyst bed volume; and
wherein at least 90% of the acetylene present in the process gas is hydrogenated, and no more than 1 mol. % of the total of acetylene and ethylene present in the process gas is converted to ethane.

Another aspect of the disclosure is method for starting up a selective hydrogenation reactor, the reactor housing one or more catalyst beds each containing a catalyst suitable for selectively hydrogenating acetylene in a process gas comprising at least 10 mol. % ethylene, at least 1 ppm acetylene, and at least 5 mol. % hydrogen, the method comprising
providing each catalyst bed at no more than a first temperature, the catalyst of the catalyst bed being in contact with a first gas, the first gas being non-reactive in the presence of the catalyst at the first temperature;
in the presence of the first gas, heating each catalyst bed to at least a second temperature, the second temperature being at least 10 degrees greater than the first temperature, the first gas being non-reactive in the presence of the catalyst at the second temperature; and then
changing the composition of the gas in contact with the catalyst from the first gas to a flow of the process gas while the catalyst bed is at least at the second temperature; and
allowing the process gas to flow through the catalyst bed until a concentration of acetylene at an outlet of the reactor is less than 1 ppm.
In certain such embodiments, the first temperature is in the range of 31-50° C., e.g., 31-45° C., or 31-40° C. In other such embodiments, the first temperature is in the range of 35-50° C., e.g., 35-45° C., or 35-40° C. And in other such embodiments, the first temperature is in the range of 40-50° C., e.g., 40-45° C., Another aspect of the disclosure is a method of starting up a selective hydrogenation reactor, the reactor housing one or more catalyst beds each containing a catalyst suitable for selectively hydrogenating acetylene in a process gas comprising at least 10 mol. % ethylene, at least 1 ppm acetylene, and at least 5 mol. % hydrogen, the method comprising;
providing the reactor with each catalyst bed having its catalyst in contact with a first gas, the first gas being non-reactive in the presence of the catalyst at the first temperature, wherein the catalyst has not been contacted in the reactor with a carbon monoxide-containing gas having a carbon monoxide concentration in excess of 100 ppm; and
introducing a flow of the process gas to the one or more catalyst beds, and refraining from adding carbon monoxide to the process gas.
Such methods can further include raising the catalyst bed temperature of each catalyst bed from no more than a first temperature to at least a second temperature (e.g., before, during or after changing the gas in contact with the catalyst from first gas to process gas).

Another aspect of the disclosure is a method of starting up a selective hydrogenation reactor, the reactor housing one or more catalyst beds each containing a catalyst suitable for selectively hydrogenating acetylene in a process gas comprising at least 10 mol. % ethylene, at least 1 ppm acetylene, and at least 5 mol. % hydrogen, the method comprising
providing each catalyst bed at no more than a first temperature, the catalyst of the catalyst bed being in contact with the gas;
in the presence of the process gas, heating each catalyst bed to at least a second temperature, the second temperature being at least 20 degrees greater than the first temperature, the heating of each catalyst bed being performed at a rate in the range of at least 3° C./hour; and
allowing the process gas to flow through the catalyst bed until a concentration of acetylene at an outlet of the reactor is less than 1 ppm.

Another aspect of the disclosure is a method of starting up a selective hydrogenation reactor, the reactor housing one or more catalyst beds each containing a catalyst suitable for selectively hydrogenating acetylene in a process gas comprising at least 10 mol. % ethylene, at least 1 ppm acetylene, and at least 5 mol. % hydrogen, the method comprising
drying the one or more catalyst beds at a temperature of at least 50 C; then
cooling each dried catalyst bed to a first temperature in the range of 31-50° C., e.g., 31-45° C., or 31-40° C., or 35-45° C., or 35-40° C., or 40-50° C., or 40-45° C.), and contacting the catalyst of each catalyst with the process gas at the first temperature; then
in the presence of the process gas, heating each catalyst bed to at least a second temperature, the second temperature being at least 20 degrees greater than the first temperature; and
allowing the process gas to flow through the catalyst bed until a concentration of acetylene at an outlet of the reactor is less than 1 ppm.

Another aspect of the disclosure is a hydrogenation catalyst composition comprising:
a porous support, present in the composition in an amount within the range of 90 wt. % to 99.9 wt. %;
palladium, present in the composition in an amount within the range of 0.02 wt. % to 0.5 wt. %, or 0.03 wt. % to 0.4 wt. %, or 0.04 wt. % to 0.3 wt. %, calculated on an elemental mass basis; and one or more ionic liquids, present in the composition in a combined amount up to 10 wt. %.

Another aspect of the disclosure is a hydrogenation catalyst composition comprising:
   a porous support, present in the composition in an amount within the range of 90 wt. % to 99.9 wt. %, having a BET surface area of no more than 10 m²/g and a pore volume of at least 0.1 mL/g;
   palladium, present in the composition in an amount within the range of at least 0.02 wt. %, calculated on an elemental mass basis; and
   one or more ionic liquids, present in the composition in a combined amount up to 10 wt. %.

Another aspect of the disclosure is a hydrogenation catalyst composition comprising:
   a porous support, present in the composition in an amount within the range of 90 wt. % to 99.9 wt. %;
   palladium, present in the composition in an amount within the range of at least 0.02 wt. %, calculated on an elemental mass basis; and
   one or more ionic liquids, present in the composition in a combined amount up to 10 wt. %,
   wherein the hydrogenation catalyst has a BET surface area of no more than 10 m²/g and a pore volume of at least 0.05 mL/g.

These hydrogenation catalyst compositions can be advantageously used in the methods described herein.

Other aspects of the disclosure will be apparent to the person of the ordinary skill in the art in view of the disclosure herein.

DETAILED DESCRIPTION

Figure 1:
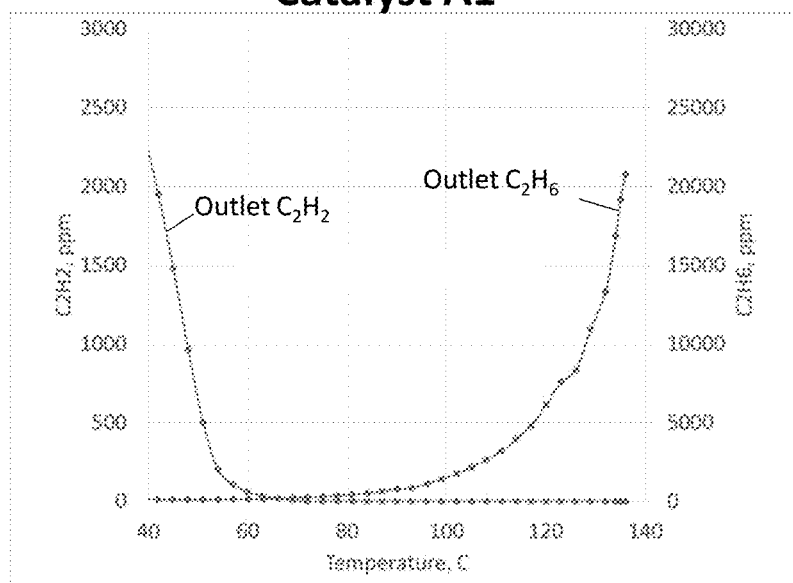
FIG. 1 is a set of graphs showing the concentration of acetylene and ethylene in the output of a process described herein (left) and the output of a conventional process (right).
Figure 1:
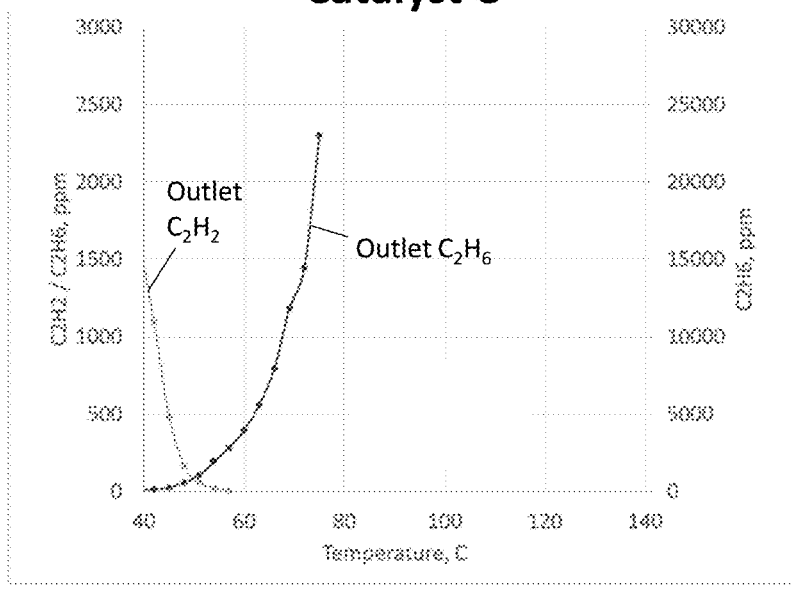

The disclosure relates to methods for selectively hydrogenating acetylene ($C_2H_2$) by contacting an acetylene-containing process gas with a catalyst composition comprising a porous support, palladium, and one or more ionic liquids, and optionally promoters such as silver, gold, zinc, tin, lead, gallium, cadmium, copper, bismuth, sodium, cesium, or potassium. The present inventors have determined that such catalysts can unexpectedly provide for improved operation of hydrogenation systems by allowing for selective hydrogenation of acetylene without thermal runaway under a wider variety of conditions than previously contemplated.

For example, in certain aspects of the disclosure, CO may be present in the process gas, if at all, in only a relatively small amount (e.g., in a range from 0 to 190 ppm, or 0 to 175 ppm, or 0 to 150 ppm, calculated on a molar basis). This can allow for processes to be performed without adding CO to a low-CO feed, simplifying operation and improving plant safety.

In other aspects, CO may be present in the process gas in a relatively large amount (e.g., at least 600 ppm, or in a range from 600 ppm to 20,000 ppm, or 600 ppm to 10,000 ppm). This can allow for high-CO process gases to be used. In various aspects, the process gas can be contacted with the catalyst composition at a relatively high gas hourly space velocity (GHSV) (e.g., at least 7,100 h⁻¹, at least 10,000 h⁻¹, or at least 12,500 h⁻¹, for example in the range of 7,100 h⁻¹ to 40,000 h⁻¹, or in the range of 10,000 h⁻¹ to 40,000 h⁻¹, or in the range of 12,500 h⁻¹ to 40,000 h⁻¹). The present inventors have determined that the catalysts described herein can be used at unexpectedly high reaction flows without runaway. And in certain embodiments, the selective hydrogenation is conducted at a relatively high temperature, allowing for increased reaction rate and increased throughput. The disclosure demonstrates that such methods of selective hydrogenation may advantageously provide desirable selective acetylene conversion and with relatively little ethylene (ethene; $C_2H_4$) conversion without thermal runaway.

Accordingly, one aspect of the disclosure is a method for selectively hydrogenating acetylene, the method comprising contacting a catalyst composition with a process gas. The catalyst composition comprises a porous support, palladium, and one or more ionic liquids. The gas mixture includes ethylene, present in the process gas in an amount of at least 15 mol. %; acetylene, present in the process gas in an amount of at least 1 ppm; hydrogen, present in the process gas in an amount of at least 5 mol. %; and 0 to 190 ppm carbon monoxide. At least 90% of the acetylene present in the process gas is hydrogenated and the selective hydrogenation is conducted without thermal runaway. And another aspect of the disclosure is a method for selectively hydrogenating acetylene, the method comprising contacting a catalyst composition with a process gas. The catalyst composition comprises a porous support, palladium, and one or more ionic liquids. The gas mixture includes ethylene, present in the process gas in an amount of at least 15 mol. %; acetylene, present in the process gas in an amount of at least 1 ppm; hydrogen, present in the process gas in an amount of at least 5 mol. %; and at least 600 ppm carbon monoxide. At least 90% of the acetylene present in the process gas is hydrogenated and the selective hydrogenation is conducted without thermal runaway. In certain such embodiments, the contacting is performed at a GHSV within the range of 2,000 h⁻¹ to 40,000 h⁻¹.

The term "thermal runaway" describes a process wherein the heat released by a catalyzed exothermic reaction (e.g., hydrogenation) increases the temperature of the catalyst, which accelerates the catalyzed reaction rate. In turn, the amount of heat released by the accelerated reaction increases, further increasing the catalyst temperature. The person of ordinary skill in the art will appreciate that, in the case of acetylene hydrogenation, this process of thermal runaway leads to increased formation of ethane ($C_2H_6$). Accordingly, as used herein, the term "thermal runaway" describes a process in which at least 90% of the acetylene present in a process gas is hydrogenated, and no more than 1 mol. % of the total acetylene and ethylene present in the process gas is converted to ethane. That is, of the acetylene present in the process gas input to the method, at least 90% of it is hydrogenated. Ethylene and acetylene are the typical components of process gases that can be over-reduced to form ethane; the present inventors have noted that the amount of this undesirable overreduction can be decreased through use of the catalysts and methods herein. Thus, "no more than 1 mol. % of the total acetylene and ethylene present in the process gas is converted to ethane" means that the amount of ethane output from the process does not increase by more than 1 mol. % based on the total content of the reactor output gas as compared to the input process gas. For example, if the input process gas stream has 20 mol. % ethane, the output stream has no more than 21 mol. % ethane.

As used herein, selectivity is defined as the portion of acetylene that is converted to ethylene, i.e., (ethylene gain)/(acetylene lost).

Another aspect of the disclosure is a method for selectively hydrogenating acetylene, the method comprising contacting a catalyst composition with a process gas at a GHSV of at least 7,100 $h^{-1}$ (e.g., within the range of 7,500 $h^{-1}$ to 40,000 $h^{-1}$). GHSV values are determined with reference to the volume of the catalyst bed(s). The catalyst composition comprises a porous support, palladium, and one or more ionic liquids. The process gas includes ethylene, present in the process gas in an amount of at least 15 mol %; acetylene, present in the process gas in an amount of at least 1 ppm; and hydrogen, present in the process gas in an amount of at least 2 mol. %. At least 90% of the acetylene present in the process gas is hydrogenated, and the selective hydrogenation is conducted without thermal runaway (i.e., no more than 1 mol. % of the total of acetylene and ethylene present in the process gas is converted to ethane). The present inventors have determined that the high selectivity of the catalysts described herein can allow for operation at unexpectedly high space volumes. In certain such embodiments, the process gas includes up to 20,000 ppm carbon monoxide.

The contacting of the process gas can be conducted using a variety of equipment familiar to a person of ordinary skill in the art. For example, the catalyst composition may be contained in one bed within a reactor vessel or divided up among a plurality of beds within a reactor. The reaction system may contain one or more reaction vessels in series. The feed to the reaction zone can flow vertically upwards, or downwards through the catalyst bed in a typical plug flow reactor, or horizontally across the catalyst bed in a radial flow type reactor. The reaction vessels can be adiabatic reactors with inter coolers, or cooled reactors, e.g. tubular isothermal reactors where catalyst is in the tubes or cooling medium is in the tubes. In some embodiments, at least 90% of the acetylene present in the process gas can be hydrogenated by contacting a catalyst composition contained in one bed. In other embodiments, at least 90% of the acetylene present in the process gas can be hydrogenated by contacting a catalyst composition divided up among a plurality of beds. The process gas can be provided as a single stream, or can be provided as multiple streams (e.g., a hydrogen stream and a hydrocarbon feed stream) that are combined in a reactor.

The present inventors have determined that, advantageously, the methods as otherwise described herein can provide beneficial performance in, for example, otherwise conventional olefin processing systems. For example, the methods as otherwise described herein can be conducted to selectively hydrogenate acetylene contained in a crude olefin stream produced by cracking (i.e., a raw-gas hydrocarbon feed), or the overhead stream of a system for separating $C_3$ hydrocarbons (i.e., a de-propanizer) or $C_2$ hydrocarbons (i.e., a de-ethanizer) from an olefin stream. In another example, the methods as otherwise described herein can be conducted to selectively hydrogenate acetylene contained in a refinery off-gas stream. Accordingly, in various embodiments as otherwise described herein, the process gas is provided from an effluent of a cracking process, from an overhead stream of a depropanizer, from an overhead stream of a de-ethanizer, or from a refinery off-gas stream.

In certain embodiments of the methods as otherwise described herein, the selective hydrogenation is conducted at a temperature within the range of 20° C. to 140° C. In certain desirable embodiments, the selective hydrogenation is conducted at a temperature within the range of 40° C. to 100° C., e.g., 40° C. to 90° C., or 50° C. to 100° C., or 50° C. to 90° C. But the processes can be conducted at a variety of temperatures. For example, in certain such embodiments, the selective hydrogenation is conducted at a temperature within the range of 20° C. to 130° C., e.g., in the range of 20° C. to 120° C., or 20° C. to 110° C., or 20° C. to 100° C., or 20° C. to 90° C. In other such embodiments, the selective hydrogenation is conducted at a temperature within the range of 40° C. to 140° C., e.g., 40° C. to 130° C., or 40° C. to 120° C., or 40° C. to 110° C. In other such embodiments, the selective hydrogenation is conducted at a temperature within the range of 50° C. to 140° C., e.g., 50° C. to 130° C., or 50° C. to 120° C., or 50° C. to 110° C. In other such embodiments, the selective hydrogenation is conducted at a temperature within the range of 60° C. to 140° C., e.g., 60° C. to 130° C., or 60° C. to 120° C., or 60° C. to 110° C., or 60° C. to 100° C., or 60° C. to 90° C.

Advantageously, the present inventors have determined that the process gas of the methods as otherwise described herein can include carbon monoxide (CO) in an amount within a relatively broad range. For example, the present inventors have noted that prior art processes typically include some amount of carbon monoxide in the process feed, going so far as to add carbon monoxide to process feeds that do not have sufficient carbon monoxide. The purpose of the carbon monoxide is to mediate the activity of the catalyst, so that the process does not run away and produce more ethane than desired. Conventional catalysts were understood to have lower selectivity for hydrogenation of acetylene, especially at lower carbon monoxide concentrations, and so addition of carbon monoxide was understood to be desirable to maintain a relatively low amount of ethane in the process output. In contrast, the present inventors have determined that the catalysts described herein can provide high selectivity without runaway even at low CO concentrations. Accordingly, in certain embodiments of the methods as otherwise described herein, CO is present in the process gas in an amount up to 190 ppm, e.g., within the range of 1 ppm to 190 ppm, for example, in the range of 5 ppm to 190 ppm, or 10 ppm to 190 ppm, or 25 ppm to 190 ppm, or 50 ppm to 190 ppm, or 100 ppm to 190 ppm. In certain embodiments of the methods as otherwise described herein, CO is present in the process gas in an amount up to 180 ppm, e.g., within the range of 1 ppm to 180 ppm, for example, in the range of 5 ppm to 180 ppm, or 10 ppm to 180 ppm, or 25 ppm to 180 ppm, or 50 ppm to 180 ppm, or 100 ppm to 180 ppm. In certain embodiments of the methods as otherwise described herein, CO is present in the process gas in an amount up to 170 ppm, e.g., within the range of 1 ppm to 170 ppm, for example, in the range of 5 ppm to 170 ppm, or 10 ppm to 170 ppm, or 25 ppm to 170 ppm, or 50 ppm to 170 ppm, or 100 ppm to 170 ppm. In certain embodiments of the methods as otherwise described herein, CO is present in the process gas in an amount up to 160 ppm, e.g., within the range of 1 ppm to 160 ppm, for example, in the range of 5 ppm to 160 ppm, or 10 ppm to 160 ppm, or 25 ppm to 160 ppm, or 50 ppm to 160 ppm, or 100 ppm to 160 ppm. In certain embodiments of the methods as otherwise described herein, CO is present in the process gas in an amount up to 150 ppm, e.g., within the range of 1 ppm to 150 ppm, for example, in the range of 5 ppm to 150 ppm, or 10 ppm to 150 ppm, or 25 ppm to 150 ppm, or 50 ppm to 150 ppm, or 100 ppm to 150 ppm. In certain embodiments of the methods as otherwise described herein, CO is present in the process gas in an amount up to 140 ppm, e.g., within the range of 1 ppm to 140 ppm, for example, in the range of 5 ppm to 140 ppm, or 10 ppm to 140 ppm, or 25 ppm to 140 ppm, or 50 ppm to 140 ppm, or 100 ppm to 140 ppm. In certain embodiments of the methods as otherwise described herein, CO is present in the process gas in an amount up to 130 ppm, e.g., within the range of 1 ppm to 130 ppm, for example, in the range of 5 ppm to 130 ppm, or 10 ppm to 130 ppm, or 25 ppm to 130 ppm, or 50 ppm to 130 ppm, or 100 ppm to 130 ppm. In certain embodiments of the methods as otherwise described herein, CO is present in the process gas in an amount up to 120 ppm, e.g., within the range of 1 ppm to 120 ppm, for example, in the range of 5 ppm to 120 ppm, or 10 ppm to 120 ppm, or 25 ppm to 120 ppm, or 50 ppm to 120 ppm. In certain embodiments of the methods as otherwise described herein, CO is present in the process gas in an amount up to 110 ppm, e.g., within the range of 1 ppm to 110 ppm, for example, in the range of 5 ppm to 110 ppm, or 10 ppm to 110 ppm, or 25 ppm to 110 ppm, or 50 ppm to 110 ppm. In certain embodiments of the methods as otherwise described herein, CO is present in the process gas in an amount up to 100 ppm, e.g., within the range of 1 ppm to 100 ppm, for example, in the range of 5 ppm to 100 ppm, or 10 ppm to 100 ppm, or 25 ppm to 100 ppm, or 50 ppm to 100 ppm. In certain embodiments of the methods as otherwise described herein, CO is present in the process gas in an amount up to 90 ppm, e.g., within the range of 1 ppm to 90 ppm, for example, in the range of 5 ppm to 90 ppm, or 10 ppm to 90 ppm, or 25 ppm to 90 ppm, or 50 ppm to 90 ppm. In certain embodiments of the methods as otherwise described herein, CO is present in the process gas in an amount up to 80 ppm, e.g., within the range of 1 ppm to 80 ppm, for example, in the range of 5 ppm to 80 ppm, or 10 ppm to 80 ppm, or 25 ppm to 80 ppm, or 50 ppm to 80 ppm. In certain embodiments of the methods as otherwise described herein, CO is present in the process gas in an amount up to 50 ppm, e.g., within the range of 1 ppm to 50 ppm, for example, in the range of 5 ppm to 50 ppm, or 10 ppm to 50 ppm, or 25 ppm to 50 ppm. In certain embodiments of the methods as otherwise described herein, essentially no CO is present in the process gas.

Notably, in certain embodiments of the methods as otherwise described herein, carbon monoxide is not added to a feed gas stream to provide the process gas. That is, unlike in many conventional methods, in certain embodiments as otherwise described herein there is no to maintain a baseline CO concentration in the process gas to maintain sufficiently low exothermicity due to ethylene hydrogenation. Rather, the catalysts described herein are highly selective to acetylene hydrogenation to ethylene, even at low CO concentrations, and so there is little risk thermal runaway due to ethylene reduction at such low CO concentrations.

The present inventors have noted that a process gas high in CO can result from variances in an upstream process step, and that continued hydrogenation performance throughout and/or after such a variance would also be desirable. The present inventors have noted that the catalysts described herein can provide continued production without runaway of in-specification gases for downstream process at high CO levels up to 20000 ppm, even in view of the significantly higher temperatures that such CO concentrations typically require (i.e., as compared to the temperatures required to cleanup acetylene at low CO levels). Notably, as described in Example 7 below, the catalysts described herein can have relatively invariant acetylene selectivity even at higher CO concentrations. In certain embodiments as otherwise described herein, CO is present in the process gas in an amount of at least 600 ppm (e.g., at least 800 ppm, or at least 1,000 ppm, or at least 1,500 ppm, or at least 2,000 ppm). For example, in certain embodiments as otherwise described herein, CO is present in the process gas in an amount within the range of 600 ppm to 20,000 ppm. For example, in certain such embodiments, CO is present in the process gas in an amount within the range of 600 ppm to 15,000 ppm, or 600 ppm to 10,000 ppm, or 600 ppm to 5,000 ppm, or 600 ppm to 2,500 ppm, or 600 ppm to 1,500 ppm, or 700 ppm to 1,200 ppm, or 800 ppm to 1,200 ppm, or 900 ppm to 1,200 ppm, or 700 ppm to 1,000 ppm, or 800 ppm to 1,100 ppm. In other such embodiments, CO is present in the process gas in an amount in the range of 800 ppm to 20,000 ppm, or 800 ppm to 15,000 ppm, or 800 ppm to 10,000 ppm, or 800 ppm to 5,000 ppm, or 800 ppm to 2,500 ppm, or 800 ppm to 1,500 ppm. In other such embodiments, CO is present in the process gas in an amount in the range of 1,000 ppm to 20,000 ppm, or 1,000 ppm to 15,000 ppm, or 1,000 ppm to 10,000 ppm, or 1,000 ppm to 5,000 ppm, or 1,000 ppm to 2,500 ppm. In other such embodiments, CO is present in the process gas in an amount in the range of 1,500 ppm to 20,000 ppm, or 1,500 ppm to 15,000 ppm, or 1,500 ppm to 10,000 ppm, or 1,500 ppm to 5,000 ppm. In other such embodiments, CO is present in the process gas in an amount in the range of 2,000 ppm to 20,000 ppm, or 2,000 ppm to 15,000 ppm, or 2,000 ppm to 10,000 ppm, or 2,000 ppm to 5,000 ppm.

However, in other embodiments, the process gas can have a different CO concentration. For example, in certain embodiments (e.g., when the GHSV is at least 7,500 $h^{-1}$, at least 10,000 $h^{-1}$, at least 15,000 $h^{-1}$ or at least 20,000 $h^{-1}$), the CO concentration of the process gas is up to 1,200 ppm, e.g., up to 1,000 ppm, or up to 500 ppm, or in the range of 10 ppm to 1,200 ppm, or in the range of 10 ppm to 500 ppm, or in the range of 50 ppm to 1,200 ppm, or in the range of 50 ppm to 500 ppm, or in the range of 100 ppm to 1,200 ppm, or in the range of 100 ppm to 500 ppm.

Advantageously, the present inventors have determined that the process gas of the methods as otherwise described herein can be contacted with the catalyst composition at a relatively high rate (e.g., at least 7,100 $h^{-1}$, or within the range of 7,500 $h^{-1}$ to 40,000 $h^{-1}$), desirably increasing throughput. The present inventors determined that as a result of the high selectivity of the catalysts described herein; advantageously, the methods described herein can be run at high throughput, while retaining selectivity and without causing runaway. Accordingly, the methods described herein can be conducted in a selective hydrogenation reactor (e.g., including a single catalyst bed, or a plurality of catalyst beds) having a relatively small volume (i.e., as compared to conventional processes to achieve the same overall rate of formation of product). Accordingly, in certain embodiments as otherwise described herein, the process gas is contacted with the catalyst at a GHSV of at least 7,100 $h^{-1}$, e.g., within the range of 7,100 $h^{-1}$ to 40,000 $h^{-1}$, or 7,100 $h^{-1}$ to 30,000 $h^{-1}$, or 7,100 $h^{-1}$ to 20,000 $h^{-1}$. In certain embodiments as otherwise described herein, the process gas is contacted with the catalyst at a GHSV of at least 7,500 $h^{-1}$, e.g., within the range of 7,500 $h^{-1}$ to 40,000 $h^{-1}$, or 7,500 $h^{-1}$ to 30,000 $h^{-1}$, or 7,500 h$^{-1}$ to 20,000 h$^{-1}$. In certain embodiments as otherwise described herein, the process gas is contacted with the catalyst at a GHSV of at least 10,000 h$^{-1}$, e.g., within the range of 10,000 h$^{-1}$ to 40,000 h$^{-1}$, or 10,000 h$^{-1}$ to 30,000 h$^{-1}$, or 10,000 h$^{-1}$ to 20,000 h$^{-1}$. In certain embodiments as otherwise described herein, the process gas is contacted with the catalyst at a GHSV of at least 15,000 h$^{-1}$, e.g., within the range of 15,000 h$^{-1}$ to 40,000 h$^{-1}$, or 15,000 h$^{-1}$ to 30,000 h$^{-1}$, or 15,000 h$^{-1}$ to 20,000 h$^{-1}$. In certain embodiments as otherwise described herein, the process gas is contacted with the catalyst at a GHSV of at least 20,000 h$^{-1}$, e.g., within the range of 20,000 h$^{-1}$ to 40,000 h$^{-1}$, or 20,000 h$^{-1}$ to 30,000 h$^{-1}$. GHSV values are determined with reference to the total volume of the catalyst bed(s).

As noted above, the processes described herein are performed such that at least 90% of the acetylene present in the process gas is hydrogenated (i.e., the acetylene conversion is at least 90%). For example, in certain embodiments of the methods as otherwise described herein, at least 92.5%, or at least 95 mol. %, or at least 96%, or at least 97%, or at least 97.5%, or at least 98%, or at least 98.5%, or at least 99% of the acetylene present in the process gas is hydrogenated. In certain embodiments of the methods as otherwise described herein, essentially all of the acetylene present in the process gas is hydrogenated.

As noted above, in various aspects, the methods as otherwise described herein can be performed without thermal runaway, i.e., no more than 1 mol. % of the total of acetylene and ethylene present in the process gas is converted to ethane. For example, in certain embodiments of the methods as otherwise described herein, no more than 0.9 mol. %, or no more than 0.8 mol. %, or no more than 0.7 mol. %, or no more than 0.6 mol. %, or no more than 0.5 mol. % of the total of acetylene and ethylene present in the process gas is converted to ethane (i.e., the amount of ethane output from the process does not increase by more than 0.8 mol. %, or 0.7 mol. %, or 0.6 mol. %, or 0.5 mol. % based on the total content of the process gas as compared to the input process gas). For example, in certain embodiments of the methods as otherwise described herein, no more than 0.2 mol. %, e.g., no more than 0.1 mol. %, or no more than 0.05 mol. %, of the total of acetylene and ethylene present in the process gas is converted to ethane. In certain embodiments of the methods as otherwise described herein, essentially none of the total of acetylene and ethylene present in the process gas is converted to ethane.

Put another way, the amount of ethane in the selectively hydrogenated product of the methods as otherwise described herein can include an amount of ethane that is no more than 1 mol. % greater than the amount of ethane in the process gas (i.e., before contacting a catalyst composition as otherwise described herein). For example, in certain embodiments, the amount of ethane in the selectively hydrogenated product of a method as otherwise described herein is no more than 0.9 mol. % greater, or no more than 0.8 mol. % greater, or no more than 0.7 mol. % greater, or no more than 0.6 mol. % greater, or no more than 0.5 mol. % greater than the amount of ethane in the process gas. In certain embodiments, the amount of ethane in the selectively hydrogenated product of a method as otherwise described herein is no more than 0.2 mol. % greater, e.g., no more than 0.1 mol. % greater, or no more than 0.05 mol. % than the amount of ethane in the process gas. In certain embodiments, the amount of ethane in the selectively hydrogenated product of a method as otherwise described herein is essentially the same as the amount of ethane in the process gas.

As described above, a wide variety of process gases can be treated using the selective hydrogenation methods described herein. For example, in certain embodiments of the methods as otherwise described herein, ethylene is present in the process gas in an amount of at least 15 mol. %. For example, in certain such embodiments, ethylene is present in the process gas in an amount in the range of 15 mol. % to 70 mol. %, or 15 mol. % to 60 mol. %, or 15 mol. % to 50 mol. %. In certain embodiments as otherwise described herein, ethylene is present in the process gas in an amount of at least 20 mol. %, e.g., in the range of 20 mol. % to 70 mol. %, or 20 mol. % to 60 mol. %, or 20 mol. % to 50 mol. %. In certain embodiments as otherwise described herein, ethylene is present in the process gas in an amount of at least 30 mol. %, e.g., in the range of 30 mol. % to 70 mol. %, or 30 mol. % to 60 mol. %, or 30 mol. % to 50 mol. %.

Acetylene can be present in the process gas composition in a variety of amounts, depending on the particular source of the process gas. In certain embodiments of the methods as otherwise described herein, acetylene is present in the process gas in an amount of at least 10 ppm, at least 50 ppm, at least 100 ppm, or at least 500 ppm, e.g., in an amount in the range of 10 ppm to 2 mol. %, or 10 ppm to 1 mol. %, or 10 ppm to 0.5 mol %, or 50 ppm to 2 mol. %, or 50 ppm to 1 mol. %, or 50 ppm to 0.5 mol %, or 100 ppm to 2 mol. %, or 100 ppm to 1 mol. %, or 100 ppm to 0.5 mol. %, or 500 ppm to 2 mol. %, or 500 ppm to 1 mol. %, or 500 ppm to 0.5 mol. %. In certain embodiments of the methods as otherwise described herein, acetylene is present in the process gas in an amount of at least 0.1 mol. %, e.g., at least 0.5 mol. % or at least 1 mol. %, e.g., in the range of 0.1 mol. % to 2 mol. %, or 0.5 mol. % to 2 mol. %, or 1 mol. % to 2 mol. %, or 0.1 mol. % to 1.5 mol. %, or 0.5 mol. % to 1.5 mol. %, or 1 mol. % to 1.5 mol. %, or 0.1 mol. % to 1 mol. %, or 0.5 mol. % to 1 mol. %.

Hydrogen can be provided in the process gas at a variety of concentrations. The person of ordinary skill in the art will select an amount of hydrogen that provides the necessary reduction of acetylene, and, for example, to provide the desired amount of hydrogen for a subsequent process step. In certain embodiments as otherwise described herein, the hydrogen is present in the process gas in an amount of at least 5 mol. %, at least 6 mol. %, at least 7 mol. %, at least 8 mol. %, at least 9 mol. %, or at least 10 mol. %, for example, in the range of 5 mol. % to 50 mol. %, or 5 mol. % to 35 mol. %, or 5 mol. % to 20 mol. %, or 5 mol. % to 15 mol. %, or 8 mol. % to 50 mol. %, or 8 mol. % to 35 mol. %, or 8 mol. % to 20 mol. %, or 8 mol. % to 15 mol. %, or 10 mol. % to 50 mol. %, or 10 mol. % to 35 mol. %, or 10 mol. % to 20 mol. %, or 10 mol. % to 15 mol. %.

The person of ordinary skill in the art will appreciate that other components may be present in the process gas of the methods as otherwise described herein. For example, the process gas can include one or more components typically present in a crude olefin stream produced by cracking such as, for example, $C_1$ components (e.g., including methane, carbon monoxide, and carbon dioxide), $C_2$ components (e.g., including ethylene, ethane, and acetylene), and $C_3$ components (e.g., including propane, propylene, propadiene, and methyl acetylene), and $C_4$ components (e.g., including 1,3-butadiene). However, in certain embodiments, the process gas will contain no more than 10 mol. % (e.g., no more than 5 mol. %, no more than 2 mol. % or no more than 1 mol. %) of carbon-containing components other than $C_1$ components (e.g., methane, carbon monoxide, and carbon dioxide), $C_2$ components (e.g., ethylene, ethane, and acetylene), and $C_3$ components (e.g., propylene, propane, methyl acetylene, and propadiene). In certain embodiments, the process gas will contain no more than 20 mol. % (e.g., no more than 15 mol. %, no more than 10 mol. % or no more than 5 mol. %) of carbon-containing components other than ethylene, ethane, acetylene, carbon monoxide and carbon dioxide. And in certain embodiments, the process gas will contain no more than 5 mol. % (e.g., no more than 2 mol. %) of carbon-containing components other than ethylene, ethane, acetylene, carbon monoxide and carbon dioxide.

Various gas streams can be combined to provide the process gas. For example, a hydrogen-containing gas stream can be added to another gas stream to provide the process gas. Gas streams can be combined in the reactor to provide the process gas that is the combination of the input gas streams.

As noted above, in various aspects, the methods of the disclosure comprise contacting a catalyst composition with a process gas. Accordingly, another aspect of the disclosure is a catalyst composition comprising a porous support, palladium, and one or more ionic liquids. In certain embodiments as otherwise described herein, the catalyst composition comprises a porous support selected from alumina, silica, titania, and any mixture thereof. In certain such embodiments, the alumina, silica, titania, and any mixture thereof are present in the catalyst composition in a total amount within the range of 90 wt. % to 99.9 wt. %, calculated as oxide on a calcined basis. For example, in certain embodiments as otherwise described herein, the catalyst composition comprises a porous support selected from alumina, silica, titania, and any mixture thereof, present in the catalyst composition in an amount within the range of 92.5 wt. % to 99 wt. %, or 95 wt. % to 99.9 wt. %, or 97.5 wt. % to 99.9 wt. %. In certain such embodiments, the porous support is a mixture of alumina and silica. In other such embodiments, the porous support is alumina, e.g., alpha-alumina.

As used herein, the term "oxide," including, e.g., "mixed oxide," "alumina," "silica," etc., includes oxides in all forms and crystalline phases. For example, "alumina" includes $Al_2O_3$, $Al_2O_x$ wherein x is within the range of 1 to 3, etc. Unless otherwise indicated, regardless of the actual stoichiometry of the oxide, oxides are calculated as the most stable oxide for purposes of weight percent determinations. For example, the person of ordinary skill in the art will appreciate that a non-stoichiometric oxide of aluminum, or even another form of aluminum, may still be calculated as $Al_2O_3$. Moreover, unless otherwise indicated, the compositions are described on an as-calcined basis.

In certain embodiments as otherwise described herein, the BET surface area of the porous support is within the range of 2 $m^2/g$ to 10 $m^2/g$. The person of ordinary skill in the art will appreciate that the "BET surface area" of a material refers to the specific surface area of a material, and is determined through the standardized testing procedure ASTM D3663 ("Standard Test Method for Surface Area of Catalysts and Catalyst Carriers"). For example, in certain embodiments as otherwise described herein, the BET surface area of the porous support is within the range of 2 $m^2/g$ to 9 $m^2/g$, or 2 $m^2/g$ to 8 $m^2/g$, or 2 $m^2/g$ to 7 $m^2/g$, or 2 $m^2/g$ to 6 $m^2/g$, or 2 $m^2/g$ to 5 $m^2/g$, or 3 $m^2/g$ to 10 $m^2/g$, or 4 $m^2/g$ to 10 $m^2/g$, or 5 $m^2/g$ to 10 $m^2/g$, or 6 $m^2/g$ to 10 $m^2/g$, or 2 $m^2/g$ to 6 $m^2/g$, or 3 $m^2/g$ to 7 $m^2/g$, or 4 $m^2/g$ to 8 $m^2/g$, or 5 $m^2/g$ to 9 $m^2/g$. BET surface areas of no more than 10 $m^2/g$ can be provided by calcining the support to a relatively high degree.

In certain embodiments as otherwise described herein, the pore volume (determined using mercury intrusion porisometry according to ASTM D4284) of the porous support is at least 0.10 mL/g, e.g., within the range of 0.10 mL/g to 1.0 mL/g. For example, in certain embodiments as otherwise described herein, the pore volume of the porous support (determined using mercury intrusion porisometry according to ASTM D4284) is within the range of 0.10 mL/g to 0.80 mL/g, or 0.20 mL/g to 0.80 mL/g, or 0.30 mL/g to 0.80 mL/g, or 0.20 mL/g to 0.70 mL/g, or 0.30 mL/g to 0.70 mL/g.

The metal-impregnated porous support (i.e., including the porous support, the palladium and any promoters present, but not the ionic liquid) can similarly have a relatively high surface area, e.g., at least of 0.10 mL/g (determined using mercury intrusion porisometry according to ASTM D4284). For example, in certain embodiments as otherwise described herein, the metal-impregnated porous support has a pore volume of at least at least 0.15 mL/g, at least 0.20 mL/g, or even 0.25 mL/g. In various embodiments as otherwise described herein, the metal-impregnated porous support has a pore volume in the range of 0.10 mL/g to 1.0 mL/g, e.g., 0.10 mL/g to 0.80 mL/g, or 0.10 to 0.60 mL/g, or 0.10 to 0.40 mL/g, or 0.10 to 0.30 mL/g. In other embodiments as otherwise described herein, the metal-impregnated porous support has a pore volume in the range of 0.15 mL/g to 1.0 mL/g, e.g., 0.15 mL/g to 0.80 mL/g, or 0.15 to 0.60 mL/g, or 0.15 to 0.40 mL/g, or 0.15 to 0.30 mL/g. In other embodiments as otherwise described herein, the metal-impregnated porous support has a pore volume in the range of 0.20 mL/g to 1.0 mL/g, e.g., 0.20 mL/g to 0.80 mL/g, or 0.20 to 0.60 mL/g, or 0.20 to 0.40 mL/g, or 0.20 to 0.35 mL/g. In other embodiments as otherwise described herein, the metal-impregnated porous support has a pore volume in the range of 0.25 mL/g to 1.0 mL/g, e.g., 0.25 mL/g to 0.80 mL/g, or 0.25 to 0.60 mL/g, or 0.25 to 0.40 mL/g, or 0.20 to 0.35 mL/g.

The present inventors have determined certain advantages when the metal-impregnated porous support also has a relatively BET low surface area (i.e., no more than 10 $m^2/g$, or a more particular range described above) together with high pore volume. Notably, in certain embodiments as otherwise described herein, the porous support has a relatively low BET surface area (i.e., no more than 10 $m^2/g$, or a more particular range described above) but a relatively high pore volume (i.e., in excess of 0.10 mL/g, e.g., within the range of 0.10 mL/g to 1.0 mL/g or a more particular range described above). This can allow for the material, after impregnation with ionic liquid as described herein, to retain some pore volume even in the presence of the ionic liquid.

For example, in certain embodiments as otherwise described herein, the catalyst composition (i.e., including the porous support, the palladium and any promoters present, and the ionic liquid) itself has a relatively high pore volume (determined using mercury intrusion porisometry according to ASTM D4284) of at least 0.05 mL/g. In certain embodiments as otherwise described herein, the catalyst composition has a pore volume of at least 0.10 mL/g, at least 0.15 mL/g, or even 0.20 mL/g. In various embodiments as otherwise described herein, the catalyst composition has a pore volume in the range of 0.05 mL/g to 1.0 mL/g, e.g., 0.05 mL/g to 0.80 mL/g, or 0.05 to 0.60 mL/g, or 0.05 to 0.40 mL/g, or 0.05 to 0.30 mL/g. In other embodiments as otherwise described herein, the catalyst composition has a pore volume in the range of 0.10 mL/g to 1.0 mL/g, e.g., 0.10 mL/g to 0.80 mL/g, or 0.10 to 0.60 mL/g, or 0.10 to 0.40 mL/g, or 0.10 to 0.30 mL/g. In other embodiments as otherwise described herein, the catalyst composition has a pore volume in the range of 0.10 mL/g to 1.0 mL/g, e.g., 0.10 mL/g to 0.80 mL/g, or 0.10 to 0.60 mL/g, or 0.10 to 0.40 mL/g, or 0.10 to 0.30 mL/g. In other embodiments as otherwise described herein, the catalyst composition has a pore volume in the range of 0.15 mL/g to 1.0 mL/g, e.g., 0.15 mL/g to 0.80 mL/g, or 0.15 to 0.60 mL/g, or 0.15 to 0.40 mL/g, or 0.15 to 0.30 mL/g. In other embodiments as otherwise described herein, the catalyst composition has a pore volume in the range of 0.20 mL/g to 1.0 mL/g, e.g., 0.20 mL/g to 0.80 mL/g, or 0.20 to 0.60 mL/g, or 0.20 to 0.40 mL/g, or 0.20 to 0.35 mL/g. Such materials can be provided by using a relatively low amount of ionic liquid, e.g., up to 4 wt. % or up to 3 wt. %, depending on the pore volume of the support.

In certain embodiments as otherwise described herein, the catalyst composition comprises palladium in an amount of at least 0.02 wt. % (i.e., calculated on an elemental mass basis). For example, in certain such embodiments, the catalyst composition comprises palladium in an amount of at least 0.03 wt. %, or at least 0.04 wt. %, or at least 0.05 wt. %, or at least 0.06 wt. %, or at least 0.07 wt. %, or at least 0.08 wt. %, or at least 0.09 wt. %, or at least 0.1 wt. %, or at least 0.11 wt. %, or at least 0.12 wt. %, or at least 0.13 wt. %, or at least 0.14 wt. %, or at least 0.15 wt. %. In certain such embodiments, the catalyst composition comprises palladium in an amount of no more than 0.5 wt. % (e.g., no more than 0.4 wt. %, or no more than 0.3 wt. %, or no more than 0.2 wt. %). For example, in certain embodiments as otherwise described herein, the catalyst composition comprises palladium in an amount within the range of 0.02 wt. % to 0.5 wt. %, or 0.02 wt. % to 0.45 wt. %, or 0.03 wt. % to 0.4 wt. %, or 0.03 wt. % to 0.35 wt. %, or 0.04 wt. % to 0.3 wt. %, or 0.04 wt. % to 0.25 wt. %.

In certain embodiments as otherwise described herein, palladium is localized at the surface of the support, in a so-called shell catalyst configuration. Materials "localized at a surface" have a substantially higher concentration (e.g., at least 100% higher) at the surface of the material (including a surface of an internal pore) than in the interior of the material. The person of ordinary skill in the art will further appreciate that the "surface" of a composition does not consist solely of the outermost surface of atoms of a composition, but rather includes a surface layer at the outside of the composition. For example, the palladium-containing shell on the support can, in certain embodiments, have a thickness up to 1 mm. The thickness of the shell is, in certain embodiments as otherwise described herein, in the range of 100-800 μm.

In certain embodiments as otherwise described herein, the catalyst composition further comprises at least one promoter selected from silver, gold, zinc, tin, lead, gallium, cadmium, copper, bismuth, sodium, cesium, or potassium. For example, in certain such embodiments, the catalyst composition comprises a silver promoter. In other such embodiments, the catalyst composition comprises a gold or zinc promoter. In certain embodiments as otherwise described herein, the at least one promoter (e.g., silver) is present in the catalyst composition in a total amount of at least 0.02 wt. % (i.e., calculated on an elemental mass basis), or least 0.04 wt. %, or at least 0.06 wt. %, or at least 0.08 wt. %, or at least 0.1 wt. % or at least 0.12 wt. %, or at least 0.14 wt. %, or at least 0.16 wt. %, or at least 0.18 wt. %, or at least 0.2 wt. %, or at least 0.22 wt. %, or at least 0.24 wt. %, or at least 0.26 wt. %, or at least 0.28 wt. %, or at least 0.3 wt. %. In certain such embodiments, the catalyst composition comprises the at least one promoter in a total amount of no more than 0.6 wt. % (e.g., no more than 0.45 wt. %, or no more than 0.3 wt. %). In certain embodiments as otherwise described herein, the at least one promoter (e.g., silver) is present together with the palladium in a shell layer. In certain embodiments, the mass ratio of palladium to promoter metal lies within a range of 1:5 to 3:1, e.g., within a range of 1:4 to 2:1, or within a range of 1:3 to 1:1.

In certain embodiments as otherwise described herein, the catalyst composition comprises at least one ionic liquid in a total amount up to 10 wt. %. For example, in certain embodiments as otherwise described herein, the catalyst composition comprises at least one ionic liquid in a total amount within the range of 0.01 wt. % to 10 wt. %, e.g., 0.01 wt. % to 8 wt. %, or 0.01 wt. % to 6 wt. %, or 0.01 wt. % to 4 wt. %, or 0.01 wt. % to 3 wt. %, or 0.01 wt. % to 2 wt. %, or 0.01 wt. % to 1 wt. %. In certain embodiments as otherwise described herein, the ionic liquid is present in an amount in the range of 0.05 wt. % to 10 wt. %, e.g., 0.05 wt. % to 8 wt. %, or 0.05 wt. % to 6 wt. %, or 0.05 wt. % to 4 wt. %, or 0.05 wt. % to 3 wt. %, or 0.05 wt. % to 2 wt. %, or 0.05 wt. % to 1 wt. %. In certain embodiments as otherwise described herein, the catalyst composition comprises at least one ionic liquid in a total amount within the range of 0.1 wt. % to 10 wt. %, e.g., 0.1 wt. % to 8 wt. %, or 0.1 wt. % to 6 wt. %, or 0.1 wt. % to 4 wt. %, or 0.1 wt. % to 3 wt. %, or 0.1 wt. % to 2 wt. %, or 0.1 wt. % to 1 wt. %. In certain embodiments as otherwise described herein, the catalyst composition comprises at least one ionic liquid in a total amount within the range of 0.2 wt. % to 10 wt. %, e.g., 0.2 wt. % to 8 wt. %, or 0.2 wt. % to 6 wt. %, or 0.2 wt. % to 4 wt. %, or 0.2 wt. % to 3 wt. %, or 0.2 wt. % to 2 wt. %, or 0.2 wt. % to 1 wt. %. In certain embodiments as otherwise described herein, the catalyst composition comprises at least one ionic liquid in a total amount within the range of 0.5 wt. % to 10 wt. %, e.g., 0.5 wt. % to 8 wt. %, or 0.5 wt. % to 6 wt. %, or 0.5 wt. % to 4 wt. %, or 0.5 wt. % to 3 wt. %, or 0.5 wt. % to 2 wt. %.

The person of ordinary skill in the art will appreciate that the term "ionic liquid" refers generally to the class of poorly coordinated salts having a relatively low melting point such as, for example, less than 100° C. In certain embodiments as otherwise described herein, the ionic liquid comprises a compound of the formula:

$$[A]_n^+[Y]_n^-$$

wherein n is 1 or 2;

$[Y]_n^-$ is selected from tetrafluoroborate ($[BF_4]^-$) hexafluorophosphate ($[PF_6]^-$); dicyanamide ($[N(CN)_2]^-$); halides ($Cl^-$, $Br^-$, $F^-$, $I^-$); hexafluoroantimonate ($[SbF_6]^-$); nitrate ($[NO_3]^-$); nitrite ($[NO_2]^-$); anionic metal complexes (e.g., $[CuCl_4]_2^-$, $[PdCl_4]_2^-$, $[AuCl_4]^-$); acetate ($[CH_3COO]^-$); trifluoracetate ($[F_3CCOO]^-$); hexafluoroarsenate ($[AsF_6]^-$); sulfate ($[SO_4]_2^-$; hydrogen sulfate ($[R'—SO_4]^-$); alkyl sulfate ($[R'—SO4]^-$); tosylate ($[C_7H_7SO_3]^-$); triflate ($[CF_3SO_3]^-$); nonaflate ($[C_4F_9SO_3]^-$); triperfluoroethylene trifluorophosphate ($[PF_3(C_2F_5)_3]^-$); tricyanomethide ($[C(CN)_3]^-$); tetracyanoborate ($[B(CN)_4]^-$; thiocyanate ($[SCN]^-$); carbonate ($[CO_3]_2$); carboxylate ($[R'—COO]^-$); sulfonate ($[R'SO_3]^-$); dialkylphosphate ($[R'PO_4R"]^-$); alkyl phosphonate ($[R'HPO_3]^-$); and bissulfonylimide ($[(R'—SO_2)_2N]^-$) (e.g., bis(trifluormethylsulfonyl) imide); wherein R' and R" are each independently linear or branched $C_1$-$C_{12}$ aliphatic or alicyclic alkyl; $C_5$-$C_{18}$ aryl; $C_5$-$C_{18}$ aryl-substituted $C_1$-$C_6$ alkyl; or $C_1$-$C_6$ alkyl-substituted $C_5$-$C_{18}$ aryl, the alkyl optionally substituted with one or more halogens;

[A]⁺ is selected from quaternary ammonium cations having the formula [NR¹R²R³R]⁺, phosphonium cations having the formula [PR¹R²R³R]⁺, sulfonium cations having the formula [SR¹R²R]+, guanidinium cations having the formula:

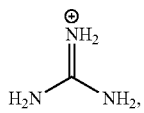

imidazolium cations having the formula:

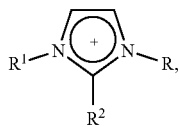

wherein the imidazole is optionally substituted with one or more groups selected from $C_1$-$C_6$ alkyl; $C_1$-$C_6$ alkoxy; $C_1$-$C_6$ aminoalkyl; $C_5$-$C_{12}$ aryl; and $C_5$-$C_{12}$ aryl-substituted $C_1$-$C_6$ alkyl; pyridinium cations having the formula:

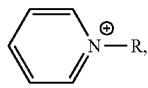

wherein the pyridine is optionally substituted with one or more groups selected from $C_1$-$C_6$ alkyl; $C_1$-$C_6$ alkoxy; $C_1$-$C_6$ aminoalkyl; $C_5$-$C_{12}$ aryl; and $C_5$-$C_{12}$ aryl-substituted $C_1$-$C_6$ alkyl; pyrazolium cations having the formula:

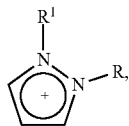

wherein the pyrazole is optionally substituted with one or more groups selected from $C_1$-$C_6$ alkyl; $C_1$-$C_6$ alkoxy; $C_1$-$C_6$ aminoalkyl; $C_5$-$C_{12}$ aryl; and $C_5$-$C_{12}$ aryl-substituted $C_1$-$C_6$ alkyl; and triazolium cations having the formula:

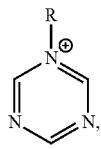

wherein the triazole is optionally substituted with one or more groups selected from $C_1$-$C_6$ alkyl; $C_1$-$C_6$ alkoxy; $C_1$-$C_6$ aminoalkyl; $C_5$-$C_{12}$ aryl; and $C_5$-$C_{12}$ aryl-substituted $C_1$-$C_6$ alkyl; wherein R¹, R², R³ are each independently hydrogen; $C_1$-$C_{20}$ alkyl; $C_3$-$C_8$ heteroaryl optionally substituted with one or more of $C_1$-$C_6$ alkyl and halogen; $C_3$-$C_6$ heteroaryl-substituted $C_1$-$C_6$ alkyl, the heteroaryl optionally substituted with one or more of $C_1$-$C_6$ alkyl and halogen; a polyether having the formula [—CH₂CH₂O]ₙR^a wherein n is within the range of 1-50,000 and R^a is selected from $C_1$-$C_{20}$ alkyl; $C_5$-$C_{12}$ aryl optionally substituted with one or more of $C_1$-$C_6$ alkyl and halogen; and $C_5$-$C_{12}$ aryl-substituted $C_1$-$C_6$ alkyl, the aryl optionally substituted with one or more of $C_1$-$C_6$ alkyl and halogen; and wherein R is selected from $C_1$-$C_{20}$ alkyl; $C_4$-$C_8$ heteroaryl-substituted $C_1$-$C_6$ alkyl, the heteroaryl optionally substituted with one or more of $C_1$-$C_6$ alkyl and halogen; and $C_4$-$C_{12}$ aryl-substituted $C_1$-$C_6$ alkyl, the aryl optionally substituted with one or more of $C_1$-$C_6$ alkyl and halogen.

For example, in certain such embodiments, $[A]_n^+$ is selected from 1-butyl-1-methylpyrrolidinium, 1-butyl-2,3-dimethylimidazolium, 1-butyl-3-methylimidazolium, 1-ethyl-3-methylimidazolium, 1-ethyl-3-methylpyridinium, 1-methyl-3-octylimidazolium, ethyldimethyl-(2-methoxyethyl)ammonium, tributylmethylammonium, tricyclohexyltetradecylphosphonium. In certain such embodiments, $[Y]_n^-$ is selected from bis(trifluoromethylsulfonyl)imide, dicyanamide, ethylsulfate, methylphosphonate, methylsulfate, octylsulfate, tetracyanoborate, tetrafluoroborate, tricyanomethane, triflate, and tris(pentafluoroethyl)trifluorophosphate.

In certain embodiments as otherwise described herein, the at least one ionic liquid is selected from 1-butyl-3-methylimidazolium triflate, 1-ethyl-3-methylpyridinium ethylsulfate, 1-butyl-1-methylpyrrolidinium triflate, 1-butyl-2,3-dimethylimidazolium triflate, 1-butyl-3-methylimidazolium tricyanomethane, 1-butyl-3-methylimidazolium methylsulfate, 1-butyl-3-methylimidazolium octylsulfate, 1-butyl-3-methylimidazolium tetrafluoroborate, 1-ethyl-3-methylimidazolium ethylsulfate, 1-ethyl-3-methylimidazolium methylphosphonate, 1-ethyl-3-methylimidazolium triflate, 1-butyl-1-methylpyrrolidinium bis(trifluoromethylsulfonyl)imide, 1-butyl-1-methylpyrrolidinium tetracyanoborate, 1-butyl-1-methylpyrrolidinium tris(pentafluoroethyl)trifluorophosphate, 1-butyl-3-methylimidazolium bis(trifluoromethylsulfonyl)imide, 1-butyl-3-methylimidazolium tricyanomethane, 1-ethyl-3-methylpyridinium bis(trifluoromethylsulfonyl)imide, 1-ethyl-3-methylimidazolium tetracyanoborate, 1-ethyl-3-methylimidazolium tris(pentafluoroethyl)trifluorophosphate, 1-methyl-3-octylimidazolium triflate, ethyldimethyl-(2-methoxyethyl)ammonium tris(pentafluoroethyl)trifluorophosphate, tributylmethylammonium dicyanamide, tricyclohexyltetradecylphosphonium tris(pentafluoroethyl)trifluorophosphate, and 1-ethyl-3-methylimidazolium bis(trifluoromethylsulfonyl)imide.

The person of ordinary skill in the art will appreciate that other components may be present in the catalyst composition as otherwise described herein. However, in certain embodiments as otherwise described herein, the total amount of porous support, palladium, promoters, and ionic liquid is at least 90 wt. %, or at least 92.5 wt. %, or at least 95 wt. %, or at least 97.5 wt. %, or at least 98 wt. %, or at least 99 wt. %, or at least 99.5 wt. %, or at least 99.9 wt. % of the catalyst composition.

The person of ordinary skill in the art will appreciate that the catalyst composition as otherwise described herein can be provided using conventional methods, e.g., by one or more impregnation steps comprising impregnating (e.g., by incipient wetness or excess solution soaking) a porous support with an impregnation solution comprising one or more ionic liquids or palladium and, optionally, a promoter (e.g., silver), each impregnation step followed by a drying or calcining step.

In certain embodiments of the production of catalyst compositions described herein, the ionic liquid or mixtures of several ionic liquids are dissolved or suspended in a solution agent suitable for the purpose, such as for example water, alcohols, acetone etc., or in a solution agent mixture, and applied continuously onto the already pre-formed catalyst inside a reaction chamber with the aid of a nozzle. For this the solution agent is continuously removed from the reaction chamber during the process. In order to achieve an even coating of the substrate, the substrate material is continuously fluidized through a process gas in a process known as fluidized bed coating. Further suitable coating processes are dip coating or spray application with a spray pistol or a spray drying pistol.

Apart from the application of ionic liquid by means of coating technologies, the same can also be applied by impregnating with a solution or suspension. For this the ionic liquid or mixtures of several ionic liquids are dissolved or suspended in a suitable solution agent (mixture) and subsequently brought into contact with the pre-formed catalyst. The solution agent is then removed under vacuum or at an increased temperature (or both), by resting in air, or by means of a gas stream. The quantity of solution agent used can be equal to or smaller or greater than the pore volume of the catalyst used.

The quantity of ionic liquid used is, in certain desirable embodiments, equal to or smaller than the pore volume of the catalyst used. After the application of the ionic liquid, one is left with an externally dry solid body coated with the desired quantity of ionic liquid. The pore volume of the resulting catalyst composition is reduced by the volume of the ionic liquid. Related to the total weight of the catalyst 0.1-10 wt. %, preferably 0.2-6 wt. %, and particularly preferably 0.3-4 wt. % of ionic liquid is used. The distribution of ionic liquid on the macroscopic substrate form body, granulate or powder is freely adjustable by selecting the coating conditions. Depending on the selection of the conditions, a formation of a so-called eggshell, egg-white, egg-yolk, or a uniform distribution of the ionic liquid may result on the substrate. In addition, any concentration gradient of ionic liquid can be created on the substrate. The ionic liquid is preferably applied to the substrate surface as a thin shell. The shell thickness of the ionic liquid on the substrate surface of the catalysts described herein usually lies within a range of 10 to 2000 μm, preferably within a range of 100 to 1000 μm, and particularly preferably within a range of 100 to 800 μm.

The resulting catalyst can be used without restricting the target reaction. The reduction of metal particles required for activating the catalyst can either take place prior to a coating with the ionic liquid or following the same.

The catalyst can for example be reduced, before or after the addition of the ionic liquid or a mixture of ionic liquids. The methods to be used for reduction are known to the expert, and can for example include wet chemical methods through a reducing agent such as for example $NaBH_4$, $LiAlH_4$, hydrazine (hydrate), hypophosphite, formic acid, or salts of the same (formates). In addition a reduction can be brought about in the gaseous phase with hydrogen (pure hydrogen or in a mixture containing hydrogen; preferably hydrogen concentration is higher than 1 mol. % in $N_2$ or other inert gases) within a temperature range of 20-200° C., preferably at 50-150° C.

The reduced metal particles obtained in this way usually have a diameter within a range of 1 to 60 nm, preferably within a range of 1 to 30 nm, and particularly preferably within a range of 2 to 20 nm.

Similarly, the hydrogenation catalyst can be reduced after the ionic liquid is provided thereon, e.g., while in a bed in a reactor, by contact with a hydrogen-containing gas as described above. For example, the ionic liquid can be impregnated onto the catalyst in a process at a catalyst synthesis site, then the catalyst can be shipped to and stored at the process site, with reduction being performed in the catalyst bed in the acetylene reduction reactor.

However, in other embodiments, the hydrogenation catalyst is not pre-reduced before contact with the process gas.

Before use, it can be advantageous to dry the catalyst to reduce the amount of any adsorbed water. Drying can be performed using a dry inert gas (e.g., nitrogen, hydrogen, residue methane, ethane) at a temperature (e.g., at at least 50° C., e.g., in the range of 50-100° C.) and for a time period (e.g., five hours to two days) until the drying gas effluent falls below a desired dew point, e.g., less than −60° C.

After any hydrogenation and drying steps, it is desirable to reduce the temperature of the catalyst to a first temperature for startup of reactive gas flow. The present inventors have determined that the catalysts described herein, as a result of their high selectivity to acetylene (and thus relatively low rate of reduction of ethylene), can be started up at a relatively higher temperature. Conventional catalysts (like Catalyst C of the Examples) were typically started up at low temperature, 30° C. or less. Notably, the present inventors have determined that the catalysts described herein can be first contacted with process gas at higher temperatures, e.g., in the range of 31-50° C. In certain embodiments, the catalysts described herein can first be contacted with process gas at a temperature in the range of 31-45° C., or 31-40° C. In other such embodiments, the catalysts described herein can first be contacted with process gas at a temperature in the range of 35-50° C., e.g., 35-45° C., or 35-40° C. And in other such embodiments, the catalysts described herein can first be contacted with process gas at a temperature in the range of 40-50° C., e.g., 40-45° C., 31-40° C., or in the range of 35-40° C.

Certain suitable catalysts for use in the methods described herein are described in U.S. Patent Application Publication no. 2013/0102819, which is hereby incorporated herein by reference in its entirety.

In various aspects and embodiments, the methods as otherwise described herein can be conducted in a selective hydrogenation reactor housing a catalyst bed or a series of catalyst beds containing a catalyst composition (e.g., a catalyst composition as otherwise described herein) capable of selectively hydrogenating acetylene.

In another aspect, the present inventors have determined that front end selective hydrogenation reactors can be started up without many of the undesirable aspects of conventional methods (e.g., long periods of time of sending process gas to flare, pre-charging of the catalyst with CO, or addition of CO to the process stream during startup), even when the catalyst composition is "fresh" (e.g., freshly installed or regenerated in the reactor, reduced or non-reduced, not yet having been exposed to a process gas). As will be appreciated by the person of ordinary skill in the art, such a startup process can desirably decrease material costs, decreases the down-time of the reactor, and decreases the waste output of the reactor (i.e., the reactor output before the reactor is fully operational).

Accordingly, another aspect of the disclosure is a method for starting up a dehydrogenation reactor, the reactor housing one or more catalyst beds each containing a catalyst suitable for selectively hydrogenating acetylene in a process gas comprising at least 10 mol. % ethylene, at least 1 ppm acetylene, and at least 5 mol. % hydrogen (e.g., and at least 10 ppm CO). The method includes providing each catalyst bed at no more than a first temperature, the catalyst of the catalyst bed being in contact with a first gas, the first gas being non-reactive in the presence of the catalyst at the first temperature. In the presence of the first gas, each catalyst bed is heated the catalyst bed to at least a second temperature, the second temperature being at least 10 degrees greater (e.g., at least 20 degrees greater, at least 30 degrees greater, at least 40 degrees greater, at least 50 degrees greater, or even at least 60 degrees greater) than the first temperature, the first gas being non-reactive in the presence of the catalyst at the second temperature. The composition of the gas in contact with the catalyst in each bed is changed from the first gas to a flow of the process gas while the catalyst bed is at least at the second temperature. The process gas is allowed to flow through each catalyst bed until a concentration of acetylene at an outlet of the reactor (i.e., that serves as the outlet for the reacted process gas) is less than 1 ppm (e.g., less than 0.5 ppm). Thus, the temperature of the catalyst bed can be increased while in contact with the first gas, such that process gas need not be diverted to flare while the catalyst beds come to temperature. In certain embodiments, the concentration of acetylene at an outlet of the reactor is no more than 1 ppm within 6 hours, e.g., within 5 hours, within 4 hours, within 3 hours or even within two hours of the process gas being introduced to the one or more catalyst beds. The catalyst materials described herein can allow for introduction of process gas while the catalyst bed(s) are at an elevated temperature, and thus reduce the amount of process gas flowing through the catalyst bed(s) during startup.

In another aspect (in combination with the aspect described above or separately), the disclosure provides a method for starting up a selective hydrogenation reactor without pre-treating the catalyst with CO and without adding CO to the process gas. For example, in one embodiment, a method of starting up a selective hydrogenation reactor as described above includes providing the reactor with each catalyst bed having its catalyst in contact with a first gas, the first gas being non-reactive in the presence of the catalyst at the first temperature, wherein the catalyst has not been contacted in the reactor with a carbon monoxide-containing gas having a carbon monoxide concentration in excess of 100 ppm. A flow of the process gas is then introduced to the one or more catalyst beds. Critically, the method includes refraining from adding carbon monoxide to the process gas. Accordingly, the method is performed without adding significant amounts of CO to the process (i.e., through a pre-treatment or by addition to the process gas). The present inventors have determined that use of the catalysts described herein can allow for start-up without carbon monoxide, which can represent significant improvements in safety, process complexity and process cost. In certain embodiments, such processes also include raising the catalyst bed temperature of each catalyst bed from no more than a first temperature to at least a second temperature. The catalyst bed temperature(s) can be raised before or after the process gas is introduced. In other embodiments, the process gas is introduced while the catalyst bed temperature(s) are raised. After the temperature is raised, process gas can be flowed through the one or more catalyst beds until a reactor effluent has less than 1 ppm acetylene (e.g., less than 0.5 ppm acetylene).

The first temperature can, for example, represent a start-up temperature of the reactor, for example, a temperature of the reactor system when it is not online. In certain embodiments, the first temperature is no more than 50° C., e.g., in the range of 31-50° C., or 35-50° C., or 40-50° C., or 45-50° C. In certain embodiments, the first temperature is no more than 45° C., e.g., in the range of 31-45° C., or 35-45° C., or 40-45° C. In certain embodiments, the first temperature is no more than 40° C., e.g., in the range of 31-40° C., or 35-40° C. But in other embodiments, the first temperature is even cooler, for example, no more than 30° C. or even, in some embodiments, no more than 25° C.

The second temperature can, for example, represent an operating temperature of the reactor, e.g., a temperature at which the reactor effluent (for the particular process gas and other conditions being used) has an acetylene concentration of no more than 1 ppm (e.g., no more than 0.5 ppm). Thus, the second temperature can be a hydrogenation reaction temperature as described above. In certain embodiments, the second temperature is within the range of 40° C. to 140° C. In certain desirable embodiments, the second temperature is within the range of 40° C. to 100° C., e.g., 40° C. to 90° C., or 50° C. to 90° C. But other second temperatures are possible. In some embodiments, the second temperature is within the range of 20° C. to 130° C., e.g., in the range of 20° C. to 120° C., or 20° C. to 110° C., or 20° C. to 100° C., or 20° C. to 90° C. In some embodiments, the second temperature is within the range of 40° C. to 140° C., e.g., 40° C. to 130° C., or 40° C. to 120° C., or 40° C. to 110° C. In some embodiments, the second temperature is within the range of 50° C. to 140° C., e.g., 50° C. to 130° C., or 50° C. to 120° C., or 50° C. to 110° C. In some embodiments, the second temperature is within the range of 60° C. to 140° C., e.g., 60° C. to 130° C., or 60° C. to 120° C., or 60° C. to 110° C., or 60° C. to 100° C., or 60° C. to 90° C. The methods described herein can be used with considerable differences between the first temperature and the second temperature, e.g., at least 30° C., at least 40° C., at least 50° C. or even at least 60° C.

The rise in temperature from no more than the first temperature to at least the second temperature can advantageously be performed relatively quickly. For example, in certain embodiments as otherwise described herein, the temperature of each catalyst bed is raised from no more than the first temperature to at least the second temperature over a time period of no more than 10 hours, e.g., no more than six hours, e.g., in the range of 2-10 hours, 4-10 hours, or 3-6 hours. The rate of temperature change can be, for example, in the range of 3-15° C./hour, e.g., in the range of 3-12° C./hour, or 6-15° C./hour, or 6-12° C./hour.

As described above, the process gas includes ethylene, acetylene and hydrogen. The process gas can have amounts of these materials and any other components as otherwise described in any embodiment herein. In certain embodiments, the process gas includes at least 10 ppm CO.

The first gas is non-reactive, as described above. In certain embodiments, the first gas includes no more than 1 ppm acetylene (e.g., no more than 0.5 ppm). A variety of substances can be used as the first gas, individually or in admixture. The first gas is non-reactive on the catalyst bed at the first temperature and the second temperature. Accordingly, the first gas can in certain embodiments include low amounts (or no) hydrogen and/or low amounts (or no) reducable hydrocarbon. In certain embodiments, the first gas includes less than 2% hydrogen, e.g., less than 1% hydrogen. Gases like nitrogen and fuel gas can be used.

In various methods described above, each catalyst bed is changed from contacting the first gas to contacting the process gas. The first gas can be present in the reactor at a relatively lower pressure than the process gas source, such that when process gas is admitted to the reactor without opening a reactor outlet, it can mix with the first gas to provide an overall reaction pressure. Desirably the difference in pressures is small enough that the process gas is significantly diluted when it is first admitted to the reactor. For example, in one example of an embodiment, the pressure of the first gas in the reactor can be 200-300 psi, while the pressure of the process gas can be 400-500 psi. Once the first gas and the process gas mix in the reactor, flow can be established by allowing gas to escape the reactor. Of course, the person of ordinary skill in the art will appreciate that the particular method of admitting the process gas to the reactor will depend on reactor and process design.

In certain desirable embodiments as otherwise described herein, the process gas itself can be used to pressure up the reactor to the reactor pressure at which the selective hydrogenation process is run. That is, in certain embodiments, there is no need to pre-pressurize with an inert gas up to the process pressure. Rather, the process gas can be used to bring the reactor up to process pressure. Advantageously, the high selectivity of the catalysts described herein allows the process gas to provide initial reactor pressure with a much reduced risk of thermal runaway.

The present inventors have determined that the catalysts described herein can be brought to process temperature more quickly than previous catalysts as a result of the high selectivity for acetylene hydrogenation. Accordingly, another aspect of the disclosure is a method of starting up a selective hydrogenation reactor, the reactor housing one or more catalyst beds each containing a catalyst suitable for selectively hydrogenating acetylene in a process gas comprising at least 10 mol. % ethylene, at least 1 ppm acetylene, and at least 5 mol. % hydrogen, the method comprising providing each catalyst bed at no more than a first temperature, the catalyst of the catalyst bed being in contact with the gas; in the presence of the process gas, heating each catalyst bed to at least a second temperature, the second temperature being at least 20 degrees greater than the first temperature, the heating of each catalyst bed being performed at a rate in the range of at least 3° C./hour; and allowing the process gas to flow through the catalyst bed until a concentration of acetylene at an outlet of the reactor is less than 1 ppm. In certain embodiments, the rate is in the range of 3-20° C./hour, e.g., 3-15° C./hour or 3-12° C./hour. In certain embodiments, the rate is in the range of 6-20° C./hour, e.g., 6-15° C./hour or 6-12° C./hour. In certain embodiments, the rate is in the range of 9-20° C./hour, e.g., 9-15° C./hour.

The catalysts described above with respect to the hydrogenation methods can be suitable for use in the startup methods described herein.

As is conventional, the methods described herein can further include, before introducing the process gas to the bed or contacting the catalyst composition with the process gas, reducing the catalyst (e.g., with a flow of a hydrogen-containing gas).

Another aspect of the disclosure is a hydrogenation catalyst composition including a porous support, present in the composition in an amount within the range of 90 wt. % to 99.9 wt. %; palladium, present in the composition in an amount within the range of 0.02 wt. % to 0.5 wt. % (e.g., 0.04 wt. % to 0.15 wt. %), calculated on an elemental mass basis; and one or more ionic liquids, present in the composition in a combined amount up to 10 wt. %. In certain embodiments, the catalyst composition further includes at least one promoter (e.g., silver), present in the composition in an amount within the range of 0.05 wt. % to 0.25 wt. %, e.g., 0.08 wt. % to 0.25 wt. %, or 0.1 wt. % to 0.25 wt. %, calculated on an elemental mass basis.

The amount of palladium in the catalyst composition can be, for example, within the range of 0.05 wt. % to 0.2 wt. %, or 0.05 wt. % to 0.15 wt. %, 0.07 wt. % to 0.2 wt. %, or 0.07 wt. % to 0.15 wt. %, or 0.08 wt. % to 0.2 wt. %, or 0.08 wt. % to 0.15 wt. %, or 0.1 wt. % to 0.2 wt. %, or 0.1 wt. % to 0.15 wt. %, or 0.11 wt. % to 0.2 wt. %, or 0.11 wt. % to 0.15 wt. %. The present inventors have determined that catalyst with relatively large amounts of palladium can usefully provide high conversion and high selectivity without runaway.

Another aspect of the disclosure is a hydrogenation catalyst composition including a porous support, present in the composition in an amount within the range of 90 wt. % to 99.9 wt. %; palladium, present in the composition in an amount of at least 0.02 wt. % (e.g., 0.04 wt. % to 0.15 wt. %), calculated on an elemental mass basis; and one or more ionic liquids, present in the composition in a combined amount up to 10 wt. %. In certain embodiments, the catalyst composition further includes at least one promoter (e.g., silver), present in the composition in an amount within the range of 0.05 wt. % to 0.25 wt. %, e.g., 0.08 wt. % to 0.25 wt. %, or 0.1 wt. % to 0.25 wt. %, calculated on an elemental mass basis. In this aspect, the support has a BET surface area of no more than 10 m$^2$/g, and a pore volume of at least 0.1 mL/g. The BET surface area and pore volume of the support can otherwise be as described above.

Another aspect of the disclosure is a hydrogenation catalyst composition including: a porous support, present in the composition in an amount within the range of 90 wt. % to 99.9 wt. %; palladium, present in the composition in an amount within the range of at least 0.02 wt. %, calculated on an elemental mass basis; and one or more ionic liquids, present in the composition in a combined amount up to 10 wt. %, wherein the hydrogenation catalyst has a BET surface area of no more than 10 m$^2$/g and a pore volume of at least 0.05 mL/g. The present inventors have determined that impregnating with relatively little ionic liquid can provide substantial pore volume remaining in the catalyst, i.e., such that pores accessible by mercury porosimetry are not completely filled.

In certain such embodiments, the hydrogenation catalyst composition comprises palladium in an amount of at least 0.03 wt. %, or at least 0.04 wt. %, or at least 0.05 wt. %, or at least 0.06 wt. %, or at least 0.07 wt. %, or at least 0.08 wt. %, or at least 0.09 wt. %, or at least 0.1 wt. %, or at least 0.11 wt. %, or at least 0.12 wt. %, or at least 0.13 wt. %, or at least 0.14 wt. %, or at least 0.15 wt. %. In certain such embodiments, the hydrogenation catalyst composition comprises palladium in an amount of no more than 0.5 wt. % (e.g., no more than 0.4 wt. %, or no more than 0.3 wt. %, or no more than 0.2 wt. %). For example, various embodiments include palladium in an amount within the range of 0.02 wt. % to 0.5 wt. %, or 0.02 wt. % to 0.45 wt. %, or 0.03 wt. % to 0.4 wt. %, or 0.03 wt. % to 0.35 wt. %, or 0.04 wt. % to 0.3 wt. %, or 0.04 wt. % to 0.25 wt. %.

Such hydrogenation catalysts can advantageously include a promoter as otherwise described herein.

In certain desirable embodiments, such hydrogenation catalysts have a BET surface area within the range of 2 m$^2$/g to 10 m$^2$/g, e.g., within the range of 2 m$^2$/g to 9 m$^2$/g, or 2 m$^2$/g to 8 m$^2$/g, or 2 m$^2$/g to 7 m$^2$/g, or 2 m$^2$/g to 6 m$^2$/g, or 2 m$^2$/g to 5 m$^2$/g, or 3 m$^2$/g to 10 m$^2$/g, or 4 m$^2$/g to 10 m$^2$/g, or 5 m$^2$/g to 10 m$^2$/g, or 6 m$^2$/g to 10 m$^2$/g, or 2 m$^2$/g to 6 m$^2$/g, or 3 m$^2$/g to 7 m$^2$/g, or 4 m$^2$/g to 8 m$^2$/g, or 5 m$^2$/g to 9 m$^2$/g.

In certain desirable embodiments, such hydrogenation catalysts have a pore volume in the range of 0.05 mL/g to 1.0 mL/g, e.g., 0.05 mL/g to 0.4 mL/g. In certain such embodiments, the hydrogenation catalyst has a pore volume in the range of 0.10 mL/g to 1.0 mL/g, e.g., 0.10 mL/g to 0.80 mL/g, or 0.10 to 0.60 mL/g, or 0.10 to 0.40 mL/g, or 0.10 to 0.30 mL/g, or in the range of 0.20 mL/g to 1.0 mL/g, e.g., 0.20 mL/g to 0.80 mL/g, or 0.20 to 0.60 mL/g, or 0.20 to 0.40 mL/g, or 0.20 to 0.35 mL/g, or in the range of 0.40 mL/g to 1.0 mL/g, e.g., 0.40 mL/g to 0.80 mL/g, or 0.40 to 0.60 mL/g.

Desirably, catalysts of the disclosure include an ionic liquid in an amount that does not completely fill the pore volume of the support. For example, in certain embodiments as otherwise described herein, the difference between the pore volume of the support and the pore volume of the catalyst (i.e., including the palladium, any promoters and the ionic liquid) is in the range of 10-90% of the pore volume of the support. In certain such embodiments, the difference is in the range of 20-90% of the pore volume of the support, e.g., 30-90% or 40-90%. In certain such embodiments, the difference is in the range of 10-80% of the pore volume of the support, e.g., 20-80%, or 30-80%, or 40-80%. In certain such embodiments, the difference is in the range of 10-70% of the pore volume of the support, e.g., 20-70%, or 30-70%, or 40-70%. In certain such embodiments, the difference is in the range of 10-60% of the pore volume of the support, e.g., 20-60%, or 30-60%, or 40-60%.

The catalysts of the disclosure can include a variety of amounts of ionic liquid. For example, in certain embodiments as otherwise described herein, the ionic liquid is present in an amount in the range of 0.1 wt. % to 10 wt. %, e.g., 0.1 wt. % to 8 wt. %, or 0.1 wt. % to 6 wt. %, or 0.1 wt. % to 4 wt. %, or 0.1 wt. % to 3 wt. %, or 0.1 wt. % to 2 wt. %, or 0.1 wt. % to 1 wt. %, e.g., 0.2 to 3 wt. %, or 0.5-4 wt. %.

The catalysts according to these aspects of the disclosure can otherwise be as described above with respect to catalysts useful in the methods of the disclosure. Moreover, the catalysts according to this aspect of the disclosure can be used in any of the methods as otherwise described herein.

The processes and materials described herein can be especially useful in front-end applications. However, the person of ordinary skill in the art will appreciate that they can be used in a variety of other applications, especially those in which risk of runaway (e.g., due to high hydrogen concentrations) is problematic.

EXAMPLES

The Examples that follow are illustrative of specific embodiments of the invention, and various uses thereof. They are set forth for explanatory purposes only, and are not to be taken as limiting the invention.

Example 1. Selective Hydrogenation Catalyst Preparation

An alpha-alumina porous support (4-mm tablets) having a BET surface area of 5±2 m²/g was impregnated by aqueous solutions of silver salt and palladium salt and calcined at minimum 260° C. in air for 2 hours. The silver content in silver salt aqueous solution and palladium content is the palladium salt solution were adjusted to make a final calcined impregnated support having 0.050±0.005 wt. % palladium and 0.070±0.005 wt. % silver. The palladium was localized within the outer 500 μm of the porous support. The pore volume of the metal-impregnated support was 0.26 mL/g.

The calcined impregnated support was further impregnated with an aqueous solution of about 0.5 wt. % of an ionic liquid (IL) on the dry impregnated support. The resulting material was dried at up to 150° C. for 2 hours to provide catalyst A1. The catalyst had a pore volume of 0.23 mL/g.

Catalyst A2 was prepared in a manner similarly to that of catalyst A1. A comparative catalyst C was also provided, which does not contain IL and has a Pd loading even less than that of catalysts A1 and A2.

TABLE 1

Catalyst Compositions

| No. | Pd (wt. %) | Ag (wt. %) | IL (wt. %) |
|---|---|---|---|
| A1 | 0.05 | 0.07 | 0.5 |
| A2 | 0.08 | 0.11 | 0.5 |
| C | 0.02 | 0.05 | 0.0 |

Example 2. Selective Hydrogenation

Catalysts prepared according to Example 1 were placed in a 15 mL catalyst bed in a reactor tube. The catalyst was reduced in a hydrogen flow with gas hourly space velocity of >500 h$^{-1}$ at 94° C. for one hour prior to introducing feed gas mixture into the reactor. A gas mixture containing 200 ppm CO, 19 mol. % H$_2$, 0.35 mol. % C$_2$H$_2$, 30 mol. % C$_2$H$_4$, 45 mol. % CH$_4$ and balance nitrogen was passed over the catalyst bed at a GHSV of 7,000 h$^{-1}$, at a total pressure of 500 psig. The catalyst bed was heated using a water bath, in intervals of 2-5° C., starting from 40° C. The concentration of acetylene and ethane were monitored at the reactor outlet, and are shown in FIG. 1. As shown in FIG. 1, the temperature at which the concentration of acetylene at the reactor outlet decreases to 25 ppm (i.e., an indicator of activity; $T_1$) is similar for catalyst A1 and C, but the operating window of catalyst A1 (i.e., the difference between the runaway temperature, $T_2$ (the temperature at which the concentration of ethane at the reactor outlet reaches 2 mol. %) and $T_1$ is significantly larger than that of catalyst C—71° C. vs. 21° C., respectively.

Example 3. CO Swing Test

Figure 2:
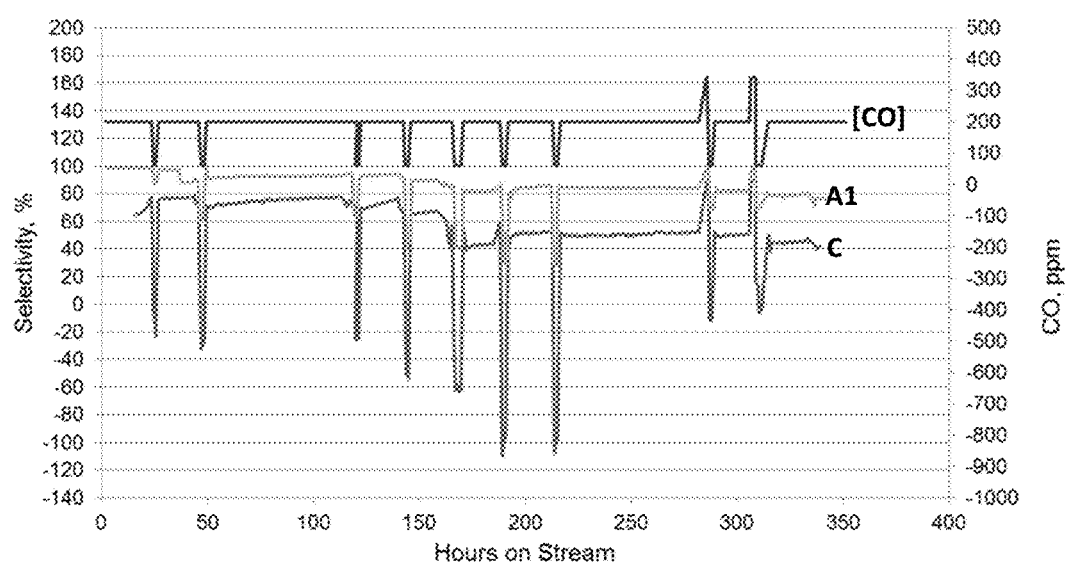
FIG. 2 is a graph showing the ethylene selectivity (left y-axis) of a process described herein (middle line) and a conventional process (bottom line) through several variations in CO concentration (top line, right y-axis).

Catalysts prepared according to Example 1 were placed in a 15 mL catalyst bed in a reactor tube. The catalyst was reduced in a hydrogen flow with gas hourly space velocity of >500 h$^{-1}$ at 94° C. for one hour prior to introducing feed gas mixture into the reactor. A gas mixture containing 200 ppm CO, 0.5 mol. % C$_2$H$_2$, 19 mol. % H$_2$, 26 mol. % C$_2$H$_4$, 40 mol. % CH$_4$ and balance nitrogen was passed over the catalyst bed at a GHSV of 7,000 h$^{-1}$. The catalyst bed was heated to a temperature sufficient to provide an acetylene concentration of 20-30 ppm at the reactor outlet. The ethylene selectivity of the process was continuously monitored at the reactor outlet, and is shown in FIG. 2.

At 25 and 45 hours on stream, the CO concentration of the gas mixture was briefly lowered to 60 ppm, without lowering the temperature of the reactor bed. At 285 hours on stream, the CO concentration of the gas mixture was increased to 340 ppm, and the temperature of the reactor bed was adjusted to provide 95% acetylene conversion. The CO concentration was subsequently lowered to 60 ppm, and then raised to 200 ppm. At 308 hours on stream, the cycle performed at 285 hours on stream was repeated. The results, shown in FIG. 2, demonstrate that the recovery of the ethylene selectivity of catalyst A1 after variations in the concentration of CO is significantly better than that of catalyst C. Moreover, the results demonstrate that the selectivity of catalyst A1 remains higher than that of catalyst C in both high and low concentrations of CO.

Example 4. Selective Hydrogenation

Figure 3:
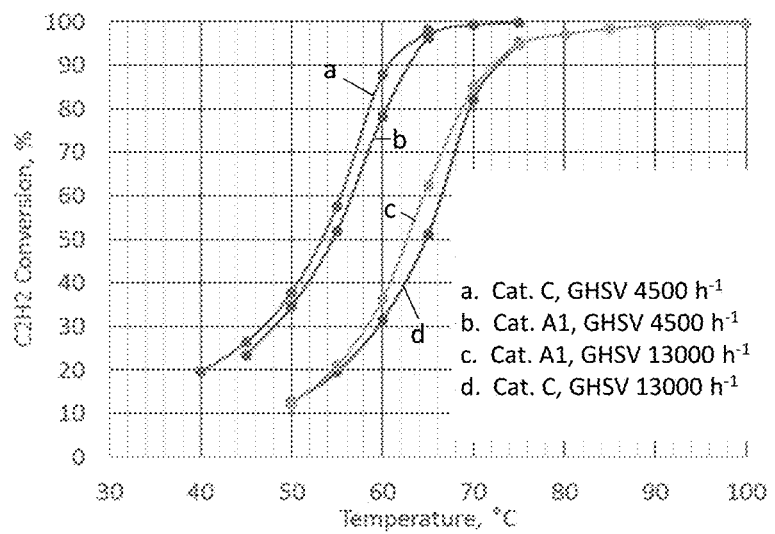
FIG. 3 is a set of graphs showing the acetylene conversion (left) and ethylene selectivity (right) of various processes described herein.
Figure 3:
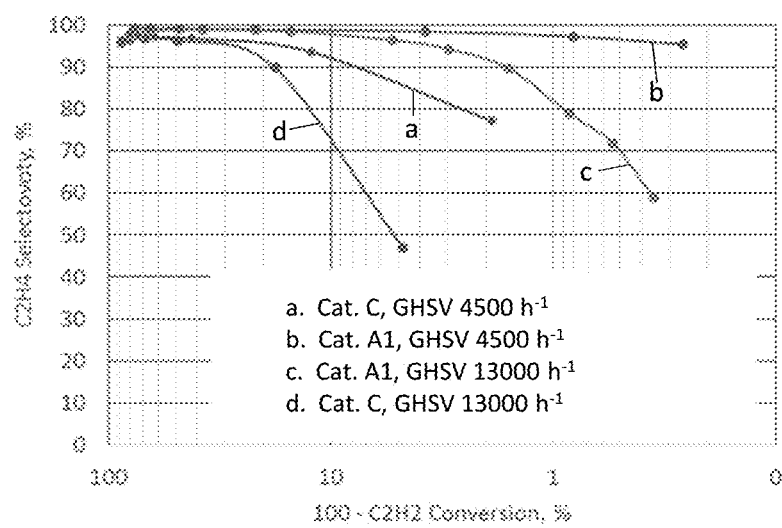

Catalysts prepared according to Example 1 were placed in a 15 mL catalyst bed in a reactor tube. The catalyst was reduced in a hydrogen flow with gas hourly space velocity of >500 $h^{-1}$ at 94° C. for one hour prior to introducing feed gas mixture into the reactor. A gas mixture containing 350 ppm CO, 17 mol. % $H_2$, 0.69 mol. % $C_2H_2$, 47 mol. % $C_2H_4$, 11 mol. % $CH_4$, 4 mol. % propylene, 0.098 ppm propadiene, 0.13 ppm methyl acetylene, and 130 ppm 1,3-butadiene was passed over the catalyst bed at a GHSV of either 4,500 $h^{-1}$ or 13,000 $h^{-1}$, at a total pressure of 500 psig. The catalyst bed was heated using a water bath, in intervals of 5° C. The acetylene conversion and ethylene selectivity were continuously monitored at the reactor outlet, and are shown in FIG. 3. Notably, the associated increase in temperature necessary to maintain a desired acetylene conversion at 13,000 $h^{-1}$ GHSV relative to 4,500 $h^{-1}$ is 10-12° C. for catalyst C, but only 8-10° C. for catalyst A1. Moreover, at 13,000 $h^{-1}$, the ethylene selectivity of catalyst A1 remained above 95% when acetylene conversion was as high as 95%, and the ethylene selectivity of catalyst A1 remained above 50% when the acetylene conversion was maintained above 99%.

Example 5. Selective Hydrogenation

Figure 4:
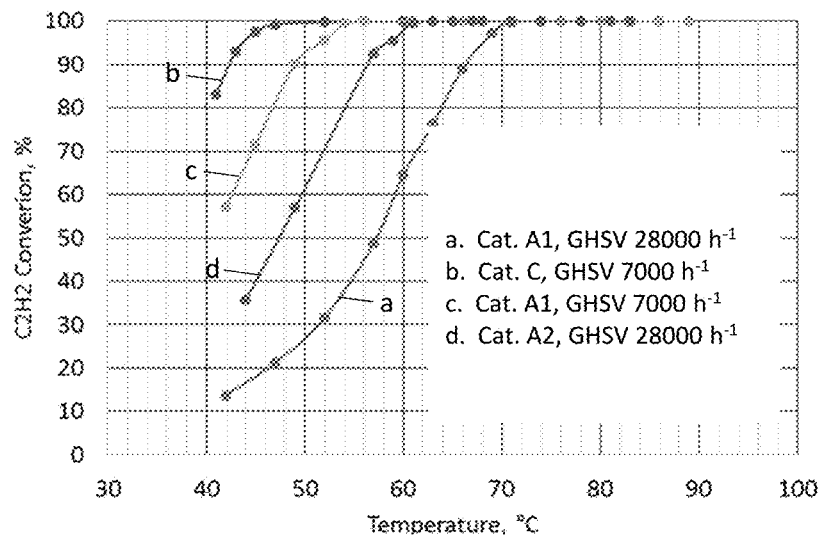
FIG. 4 is a set of graphs showing the acetylene conversion (left) and ethylene selectivity (right) of various processes described herein.
Figure 4:
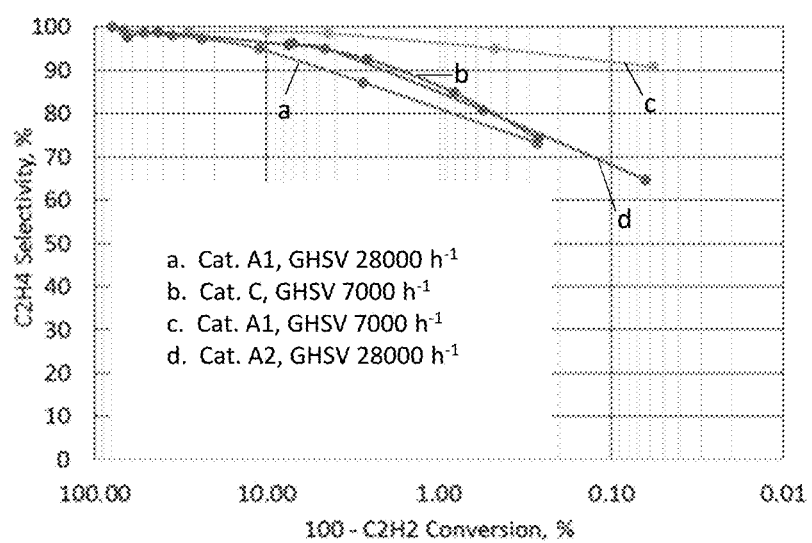

Catalysts prepared according to Example 1 were placed in a 15 mL catalyst bed in a reactor tube. The catalyst was reduced in a hydrogen flow with gas hourly space velocity of >500 $h^{-1}$ at 94° C. for one hour prior to introducing feed gas mixture into the reactor. A gas mixture containing 200 ppm CO, 19 mol. % $H_2$, 0.35 mol. % $C_2H_2$, 30 mol. % $C_2H_4$, 45 mol. % $CH_4$ and balance nitrogen was passed over the catalyst bed at a GHSV of either 7,000 $h^{-1}$ or 28,000 $h^{-1}$, at a total pressure of 500 psig. The catalyst bed was heated using a water bath, in intervals of 2-5° C., starting from 40° C. The acetylene conversion and ethylene selectivity were continuously monitored at the reactor outlet, and are shown in FIG. 4. Notably, the ethylene selectivity of catalyst A2 at 28,000 $h^{-1}$ was similar to that of catalyst C at only 7,000 $h^{-1}$, i.e., the process capacity was about 4 times higher for catalyst A2.

Example 6. Reactor Startup without CO Pre-Treatment

Commercial Front End selective hydrogenation plants typically require pre-treatment of the catalyst bed with CO at start-up to prevent the reactor temperature from runaway when process gas is first introduced to the reactor due to non-selective hydrogenation of ethylene to ethane.

A series of start-up tests were performed in a laboratory-scale test unit using catalyst A1 without CO pre-treatment and compared to the base case with CO gas pre-treatment of the catalyst. Tests were run at GHSV values of 7000 $h^{-1}$.

Figure 5:
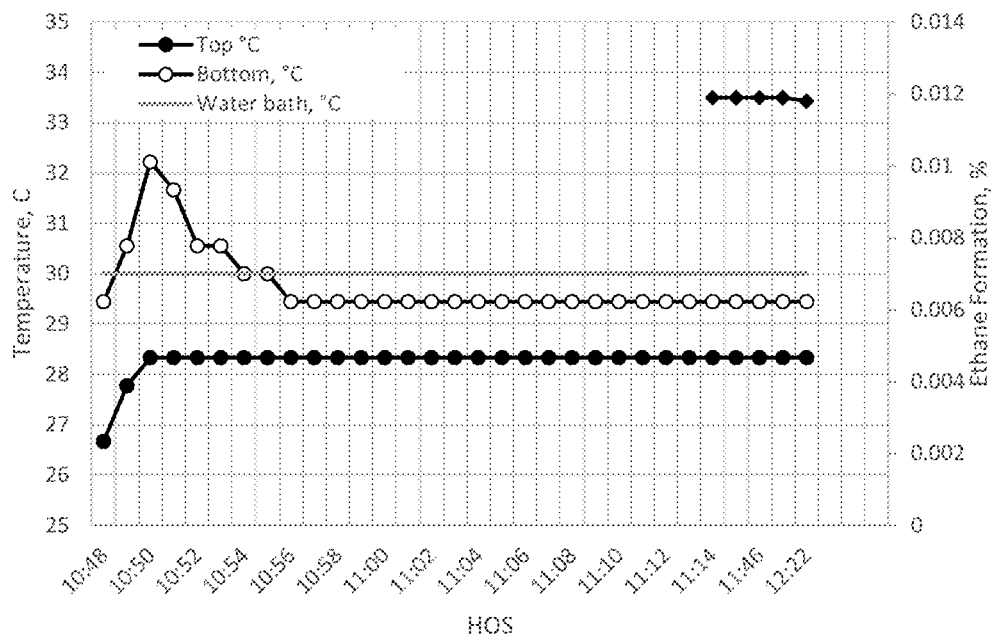
FIGS. 5, 6, 7 and 8 are graphs of reactor temperatures for the startup experiments of Example 6.

The comparative start-up process in the laboratory-scale test included a $H_2$ reduction at 94° C. for 1 hour followed by a CO pre-treatment purge prior to bringing all feed gases on stream. In this comparative test, 1% CO in $CH_4$ gas was used to purge the system for 20 minutes at 30° C. and to pressurize the reactor to 35 bar, then the feed gas containing 0.02% CO, 20% $H_2$, 3500 ppm $C_2H_2$, and 27% $C_2H_4$ was bought on stream at 35 bar. The water bath temperature remained at 30° C., while catalyst bed top and bottom temperatures were monitored during the test. Data are shown in FIG. 5. The first temperature point was when the pressure-up began with just the CO/$CH_4$ gas. The pressure-up with CO/$CH_4$ took over 1-2 minutes. Initially, there was a brief 2-3° C. exotherm for ~5 min. The introduction of feed gas at 30° C. and 35 bar did not cause a significant exotherm. Reactor outlet gas sample was analysed at 15 minutes after catalyst bed temperatures were stable. The outlet ethane concentration was stable at 120 ppm, which was from inlet feed.

Figure 6:
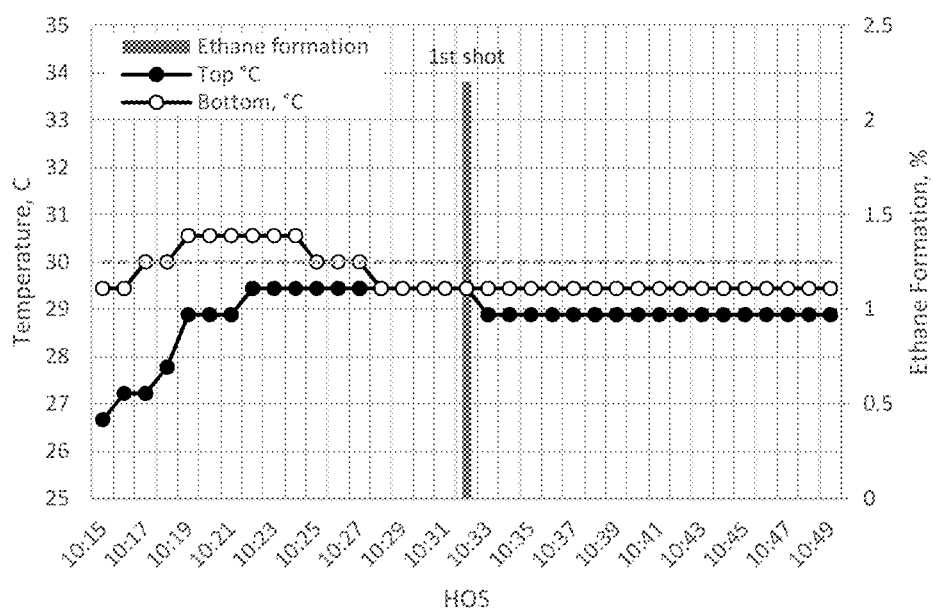

Next, the start-up test was repeated in substantially the same manner, but replacing the CO/$CH_4$ pretreatment with an $N_2$ pre-treatment, followed by introducing feed gas at atmosphere pressure and pressurizing the reactor using feed gas at the flow rate of 7000 h−1 GHSV. The water bath temperature remained at 30° C., top and bottom temperatures were monitored during the test. It took ~10 min reach the 35 bar target pressure. Data are shown in FIG. 6.

During the 10 min the of pressure-up period, a 2 to 3° C. exotherm was observed, and both top and bottom temperatures returned to below 30° C. after gas flow was stabilized at 35 bar, when a gas sample of reactor outlet was analysed showing in excess of 2% ethane. This initial ethane formation was due to the fact that there was no flow from reactor during pressure-up before the reactor reaching 35 bar. Continuous analysis of outlet sample after inlet and outlet flow were stabilized at 35 bar showed that the ethane content at reactor outlet dropped to about 120 ppm, indicating no sustained formation of ethane in the reactor.

Figure 7:
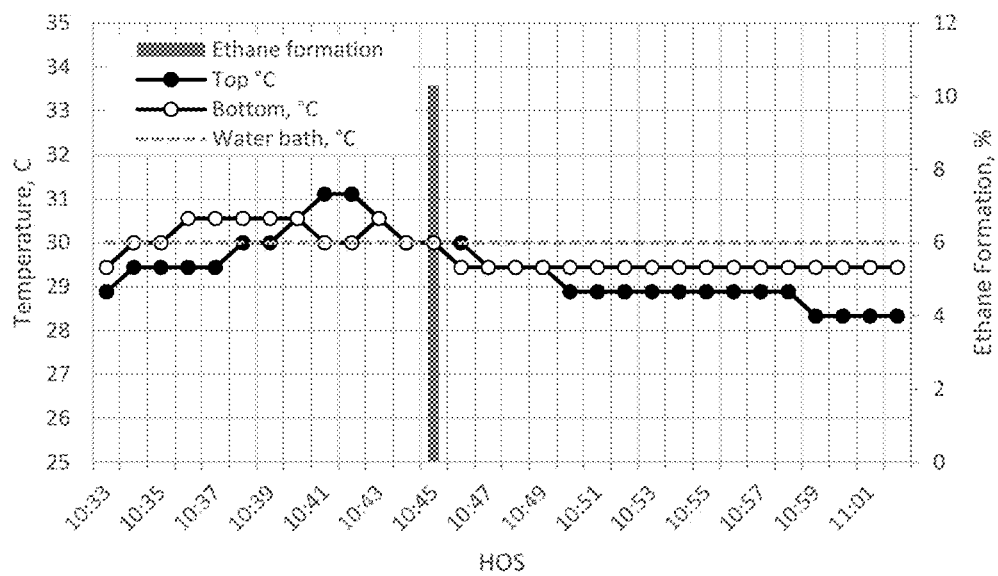

Another start-up test was performed, this time, omitting the $N_2$ purge between the hydrogen reduction and introduction of the feed gas. Instead, the catalyst was purged with feed gas containing 0.02% CO, 20% $H_2$, 3500 ppm $C_2H_2$, and 27% $C_2H_4$ CO, for 20 minutes before being pressured up to 35 bar with the feed gas. This was done to simulate recirculation of gases prior to start-up in plant conditions. Temperature measurements started at the beginning of the pressure-up; data is shown in FIG. 7. No temperature change was noticed during the 20 min feed purge. Both top and bottom temperatures started to increase during the pressure-up and top temperature exceed the bottom temperature slightly. Ethane formation during this temperature spike was around 10%. Temperatures eventually returned to normal after 10 min. Ethane formation continued to decline throughout the test until becoming stable at 120 ppm.

Figure 8:
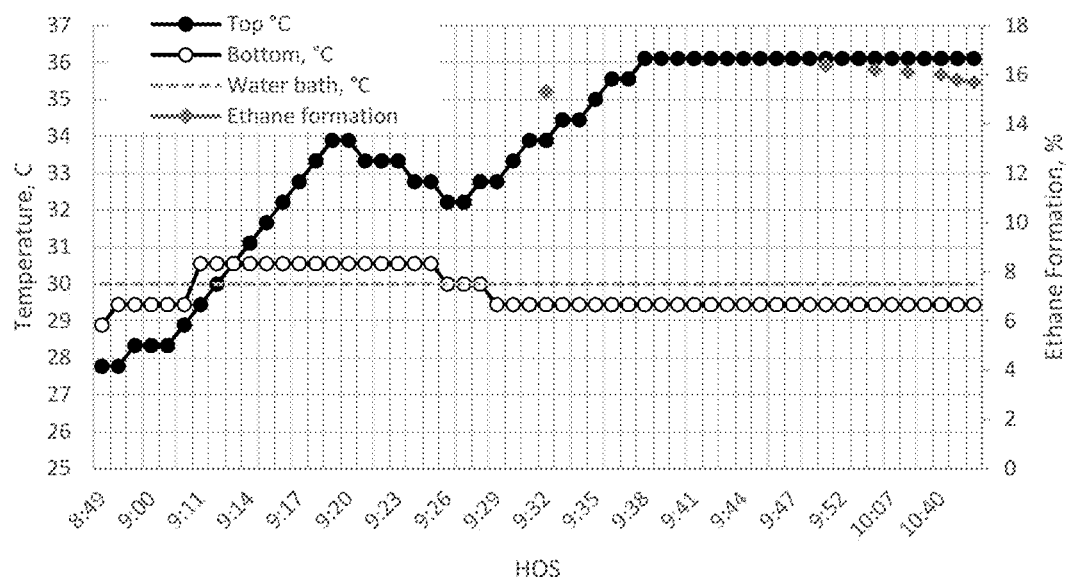
Figure 9:
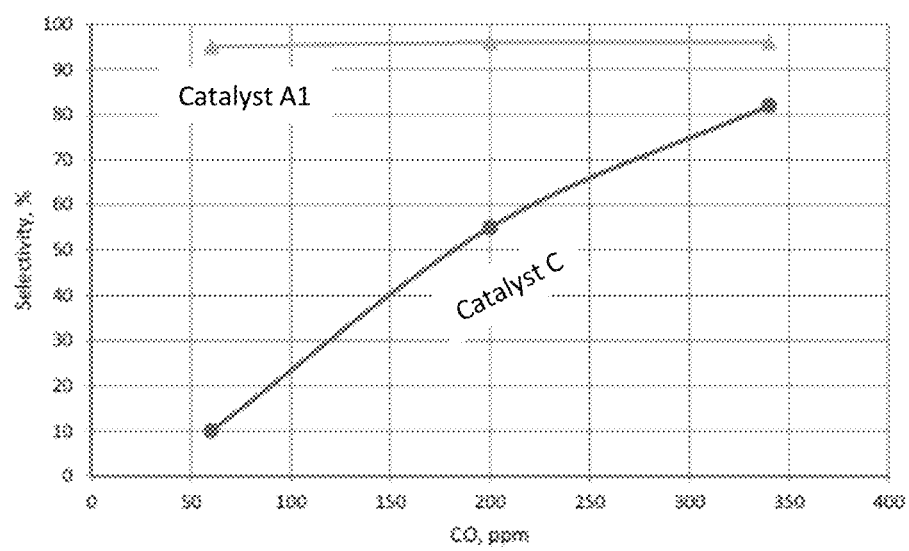
FIG. 9 is a graph of acetylene reduction selectivity with respect to CO concentration under isothermal conditions for a catalyst as described herein and a comparative catalyst.

Finally, the start-up procedure using feed gas to purge as described above was applied to catalyst C. FIG. 8 shows that catalyst bed temperature change and ethane formation during the start-up test. The temperature measurements started at once feed is introduced. The top temperature started to increase before pressure-up, exceeding the bottom temperature at the beginning of pressure-up. The top temperature dropped slightly after pressure-up and continuous gas flow was established, but then continued to increases until stabilizing at 36° C. The top temperature did not return to below 30°. The ethane formation during this time was stable at ~16%, indicating sustained thermal runaway.

Thus, the start-up experiments described above demonstrate that catalysts including ionic liquids can provide a low risk of thermal runaway, even in the absence of CO pre-treatment.

Example 7. Insensitivity to Carbon Monoxide Concentration

A study of sensitivity to carbon monoxide concentration was performed under isothermal conditions. Notably, the selectivity of Catalyst A1 was relatively insensitive to carbon monoxide concentration, while the sensitivity of Catalyst C was much more sensitive to carbon monoxide concentrations. In adiabatic systems, an increased exotherm from increased ethylene hydrogenation at lower CO concentrations even further decreases the selectivity, potentially triggering exothermic runaway. Notably, these data demonstrate that the catalysts described herein can be used under a wide variety of conditions even at low CO concentrations.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice. Thus, before the disclosed processes and devices are described, it is to be understood that the aspects described herein are not limited to specific embodiments, apparatuses, or configurations, and as such can, of course, vary. It is also to be understood that the terminology used herein is for the purpose of describing particular aspects only and, unless specifically defined herein, is not intended to be limiting.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All methods described herein can be performed in any suitable order of steps unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range within normal ranges of uncertainty and imprecision in the art.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Some embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Additional embodiments of the disclosure are provided by the enumerated embodiments below, which can be combined in any number and in any fashion that is logically and technically consistent.

Embodiment 1

A method for selectively hydrogenating acetylene, the method comprising contacting a catalyst composition comprising a porous support, palladium, and at least one ionic liquid with a process gas comprising
 ethylene, present in the process gas in an amount of at least 10 mol. %;
 acetylene, present in the process gas in an amount of at least 1 ppm;
 hydrogen, present in the process gas in amount of at least 5 mol. %; and 0 ppm to 190 ppm carbon monoxide;
wherein at least 90% of the acetylene present in the process gas is hydrogenated, and no more than 1 mol. % of the total of acetylene and ethylene present in the process gas is converted to ethane.

Embodiment 2

A method for selectively hydrogenating acetylene, the method comprising contacting a catalyst composition comprising a porous support, palladium, and at least one ionic liquid with a process gas comprising
 ethylene, present in the process gas in an amount of at least 10 mol. %;
 acetylene, present in the process gas in an amount of at least 1 ppm;
 hydrogen, present in the process gas in amount of at least 5 mol. %; and at least 600 ppm carbon monoxide;
wherein at least 90% of the acetylene present in the process gas is hydrogenated, and no more than 1 mol. % of the total of acetylene and ethylene present in the process gas is converted to ethane.

Embodiment 3

A method according to Embodiment 1 or 2, wherein the process gas is contacted with the catalyst at a gas hourly space velocity (GHSV) within the range of 2,000 h$^{-1}$ to 40,000 h$^{-1}$.

Embodiment 4

A method for selectively hydrogenating acetylene, the method comprising contacting a catalyst composition comprising a porous support, palladium, and one or more ionic liquids with a process gas comprising
 ethylene, present in the process gas in an amount of at least 10 mol. %;
 acetylene, present in the process gas in an amount of at least 1 ppm; and
 hydrogen, present in the process gas in an amount of at least 5 mol. %;
wherein the process gas is contacted with the catalyst at a gas hourly space velocity (GHSV) based on total catalyst bed volume (i.e., in one bed or multiple beds) of at least 7,100 h$^{-1}$ (e.g., 7,500 h$^{-1}$ to 40,000 h$^{-1}$); and
wherein at least 90% of the acetylene present in the process gas is hydrogenated, and no more than 1 mol. % of the total of acetylene and ethylene present in the process gas is converted to ethane.

Embodiment 5

A method according to claim 4, wherein carbon monoxide is present in the process gas in an amount up to 20,000 ppm, e.g., up to 10,000 ppm, or up to 5,000 ppm, or up to 2,500 ppm, or up to 1,200 ppm, or up to 1,000 ppm.

Embodiment 6

A method according to claim 4, wherein carbon monoxide is present in the process gas in an amount up to 100 ppm, or up to 500 ppm, or up to 1,000 ppm, or up to 5,000 ppm, or in the range of 10 ppm to 5,000 ppm, or in the range of 10 ppm to 1,200 ppm, or in the range of 10 ppm to 500 ppm, or in the range of 50 ppm to 5,000 ppm, or in the range of 50 ppm to 1,200 ppm, or in the range of 50 ppm to 500 ppm, or in the range of 75 ppm to 1,200 ppm, or in the range of 75 ppm to 500 ppm.

Embodiment 7

A method according to any of embodiments 1, 3 and 4, wherein carbon monoxide is present in the process gas in an amount up to 190 ppm, e.g., up to 175 ppm, or within the range of 1 ppm to 190 ppm, or in the range of 5 ppm to 190 ppm, or 10 ppm to 190 ppm, or 25 ppm to 190 ppm, or 50 ppm to 190 ppm, or 75 ppm to 190 ppm, or 1 ppm to 175 ppm, or 5 ppm to 175 ppm, or 10 ppm to 175 ppm, or 25 ppm to 175 ppm, or 50 ppm to 175 ppm, or 100 ppm to 175 ppm.

Embodiment 8

A method according to any of embodiments 1, 3 and 4, wherein carbon monoxide is present in the process gas in an amount up to 150 ppm, for example, up to 140 ppm, e.g., within the range of 1 ppm to 150 ppm, or 5 ppm to 150 ppm, or 10 ppm to 150 ppm, or 25 ppm to 150 ppm, or 50 ppm to 150 ppm, or 75 ppm to 150 ppm, or 1 ppm to 140 ppm, or 5 ppm to 140 ppm, or 10 ppm to 140 ppm, or 25 ppm to 140 ppm, or 50 ppm to 140 ppm, or 75 ppm to 140 ppm.

Embodiment 9

A method according to any of embodiments 1, 3 and 4, wherein carbon monoxide is present in the process gas in an amount up to 125 ppm, for example, up to 115 ppm, e.g., within the range of 1 ppm to 125 ppm, or 5 ppm to 125 ppm, or 10 ppm to 125 ppm, or 25 ppm to 125 ppm, or 50 ppm to 125 ppm, or 75 ppm to 125 ppm, or 1 ppm to 115 ppm, or 5 ppm to 115 ppm, or 10 ppm to 115 ppm, or 25 ppm to 115 ppm, or 50 ppm to 115 ppm, or 75 ppm to 115 ppm.

Embodiment 10

A method according to any of embodiments 1, 3 and 4, wherein carbon monoxide is present in the process gas in an amount up to 110 ppm, for example, up to 100 ppm, e.g., within the range of 1 ppm to 110 ppm, or 5 ppm to 110 ppm, or 10 ppm to 110 ppm, or 25 ppm to 110 ppm, or 50 ppm to 110 ppm, or 75 ppm to 110 ppm, or 1 ppm to 100 ppm, or 5 ppm to 100 ppm, or 10 ppm to 100 ppm, or 25 ppm to 100 ppm, or 50 ppm to 100 ppm.

Embodiment 11

A method according to any of embodiments 1, 3 and 4, wherein carbon monoxide is present in the process gas in an amount up to 95 ppm, for example, up to 90 ppm, e.g., within the range of 1 ppm to 95 ppm, or 5 ppm to 95 ppm, or 10 ppm to 95 ppm, or 25 ppm to 95 ppm, or 50 ppm to 95 ppm, or 1 ppm to 90 ppm, or 5 ppm to 90 ppm, or 10 ppm to 90 ppm, or 25 ppm to 90 ppm, or 50 ppm to 90 ppm.

Embodiment 12

A method according to any of embodiments 1, 3 and 4, wherein carbon monoxide is present in the process gas in an amount up to 85 ppm, for example, up to 80 ppm, e.g., within the range of 1 ppm to 85 ppm, or 5 ppm to 85 ppm, or 10 ppm to 85 ppm, or 25 ppm to 85 ppm, or 50 ppm to 85 ppm, or 1 ppm to 80 ppm, or 5 ppm to 80 ppm, or 10 ppm to 80 ppm, or 25 ppm to 80 ppm, or 50 ppm to 80 ppm.

Embodiment 13

A method according to any of embodiments 1-12, wherein carbon monoxide is not added to a feed gas stream to provide the process gas.

Embodiment 14

A method according to any of embodiments 2-4, wherein carbon monoxide is present in the process gas in an amount within the range of 600 ppm to 20,000 ppm, or 600 ppm to 15,000 ppm, or 600 ppm to 12,500 ppm, or 700 ppm to 10,000 ppm, or 800 ppm to 7,500 ppm, or 900 ppm to 5,000 ppm, or 700 ppm to 5,000 ppm, or 800 ppm to 5,000 ppm.

Embodiment 15

A method according to any of embodiments 2-4, wherein carbon monoxide is present in the process gas in an amount within the range of 800 ppm to 20,000 ppm, or 800 ppm to 15,000 ppm, or 800 ppm to 10,000 ppm, or 800 ppm to 5,000 ppm, or 800 ppm to 2,500 ppm, or 800 ppm to 1,500 ppm.

Embodiment 16

A method according to any of embodiments 2-4, wherein carbon monoxide is present in the process gas in an amount within the range of 1,000 ppm to 20,000 ppm, or 1,000 ppm to 15,000 ppm, or 1,000 ppm to 10,000 ppm, or 1,000 ppm to 5,000 ppm, or 1,000 ppm to 2,500 ppm.

Embodiment 17

A method according to any of embodiments 2-4, wherein carbon monoxide is present in the process gas in an amount within the range of 1,500 ppm to 20,000 ppm, or 1,500 ppm to 15,000 ppm, or 1,500 ppm to 10,000 ppm, or 1,500 ppm to 5,000 ppm.

Embodiment 18

A method according to any of embodiments 2-4, wherein carbon monoxide is present in the process gas in an amount within the range of 2,000 ppm to 20,000 ppm, or 2,000 ppm to 15,000 ppm, or 2,000 ppm to 10,000 ppm, or 2,000 ppm to 5,000 ppm.

Embodiment 19

A method according to any of embodiments 1, 2 and 4-18, wherein the process gas is contacted with the catalyst at a GHSV of at least 7,100 $h^{-1}$, e.g., within the range of 7,100 $h^{-1}$ to 40,000 $h^{-1}$, or 7,100 $h^{-1}$ to 30,000 $h^{-1}$, or 7,100 $h^{-1}$ to 20,000 $h^{-1}$.

Embodiment 20

A method according to any of embodiments 1, 2 and 4-18, wherein the process gas is contacted with the catalyst at a GHSV of at least 7,500 $h^{-1}$, e.g., within the range of 7,500 $h^{-1}$ to 40,000 $h^{-1}$, or 7,500 $h^{-1}$ to 30,000 $h^{-1}$, or 7,500 $h^{-1}$ to 20,000 $h^{-1}$.

Embodiment 21

A method according to any of embodiments 1, 2 and 4-18, wherein the process gas is contacted with the catalyst at a GHSV of at least 10,000 $h^{-1}$, e.g., within the range of 10,000 $h^{-1}$ to 40,000 $h^{-1}$, or 10,000 $h^{-1}$ to 30,000 $h^{-1}$, or 10,000 $h^{-1}$ to 20,000 $h^{-1}$.

Embodiment 22

A method according to any of embodiments 1, 2 and 4-18, wherein the process gas is contacted with the catalyst at a GHSV of at least 12,500 $h^{-1}$, e.g., within the range of 12,500 $h^{-1}$ to 40,000 $h^{-1}$, or 12,500 $h^{-1}$ to 30,000 $h^{-1}$, or 12,500 $h^{-1}$ to 20,000 $h^{-1}$.

Embodiment 23

A method according to any of embodiments 1, 2 and 4-18, wherein the process gas is contacted with the catalyst at a GHSV of at least 15,000 $h^{-1}$, e.g., within the range of 15,000 $h^{-1}$ to 40,000 $h^{-1}$, or 15,000 $h^{-1}$ to 30,000 $h^{-1}$, or 15,000 $h^{-1}$ to 20,000 $h^{-1}$.

Embodiment 24

A method according to any of embodiments 1, 2 and 4-18, wherein the process gas is contacted with the catalyst at a GHSV of at least 20,000 $h^{-1}$, e.g., within the range of 20,000 $h^{-1}$ to 40,000 $h^{-1}$, or 20,000 $h^{-1}$ to 30,000 $h^{-1}$.

Embodiment 25

A method according to any of embodiments 1-24, wherein the selective hydrogenation is conducted at a temperature within the range of 20° C. to 140° C.

Embodiment 26

A method according to any of embodiments 1-24, wherein the selective hydrogenation is conducted at a temperature within the range of 40° C. to 100° C.

Embodiment 27

A method according to any of embodiments 1-24, wherein the selective hydrogenation is conducted at a temperature within the range of 40° C. to 90° C.

Embodiment 28

A method according to any of embodiments 1-24, wherein the selective hydrogenation is conducted at a temperature within the range of 50° C. to 90° C.

Embodiment 29

A method according to any of embodiments 1-24, wherein the selective hydrogenation is conducted at a temperature within the range of 50° C. to 100° C.

Embodiment 30

A method according to any of embodiments 1-24, wherein the selective hydrogenation is conducted at a temperature within the range of 20° C. to 130° C., e.g., in the range of 20° C. to 120° C., or 20° C. to 110° C., or 20° C. to 100° C., or 20° C. to 90° C.

Embodiment 31

A method according to any of embodiments 1-24, wherein the selective hydrogenation is conducted at a temperature within the range of 40° C. to 140° C., e.g., 40° C. to 130° C., or 40° C. to 120° C., or 40° C. to 110° C.

Embodiment 32

A method according to any of embodiments 1-24, wherein the selective hydrogenation is conducted at a temperature within the range of 50° C. to 140° C., e.g., 50° C. to 130° C., or 50° C. to 120° C., or 50° C. to 110° C.

Embodiment 33

A method according to any of embodiments 1-24, wherein the selective hydrogenation is conducted at a temperature within the range of 60° C. to 140° C., e.g., 60° C. to 130° C., or 60° C. to 120° C., or 60° C. to 110° C., or 60° C. to 100° C., or 60° C. to 90° C.

Embodiment 34

A method according to any of embodiments 1-33, wherein at least 95% of the acetylene present in the process gas is hydrogenated, e.g., at least 96%, or at least 97%, or at least 97.5% of the acetylene present in the process gas is hydrogenated.

Embodiment 35

A method according to any of embodiments 1-33, wherein at least 98% of the acetylene present in the process gas is hydrogenated, e.g., at least 98.5%, or at least 99% of the acetylene present in the process gas is hydrogenated.

Embodiment 36

A method according to any of embodiments 1-33, wherein essentially all of the acetylene present in the process gas is hydrogenated.

Embodiment 37

A method according to any of embodiments 1-36, wherein the amount of ethane in the product of the selective hydrogenation is no more than 1 mol. % greater than the amount of ethane in the process gas.

Embodiment 38

A method according to any of embodiments 1-36, wherein the amount of ethane in the product of the selective hydrogenation is no more than 0.9 mol. %, e.g., no more than 0.8 mol. % greater than the amount of ethane in the process gas.

Embodiment 39

A method according to any of embodiments 1-36, wherein the amount of ethane in the product of the selective hydrogenation is no more than 0.7 mol. %, e.g., no more than 0.6 mol. % greater than the amount of ethane in the process gas.

Embodiment 40

A method according to any of embodiments 1-36, wherein the amount of ethane in the product of the selective hydrogenation is no more than 0.5 mol. % greater than the amount of ethane in the process gas.

Embodiment 41

A method according to any of embodiments 1-36, wherein the amount of ethane in the product of the selective hydrogenation is no more than 0.2 mol. % greater than the amount of ethane in the process gas.

Embodiment 42

A method according to any of embodiments 1-36, wherein the amount of ethane in the product of the selective hydrogenation is no more than 0.1 mol. % greater than the amount of ethane in the process gas.

Embodiment 43

A method according to any of embodiments 1-36, wherein the amount of ethane in the product of the selective hydrogenation is no more than 0.05 mol. % greater than the amount of ethane in the process gas.

Embodiment 44

A method according to any of embodiments 1-44, wherein ethylene is present in the process gas in an amount in the range of 10 mol. % to 70 mol. %, or 15 mol. % to 60 mol. %, or 15 mol. % to 50 mol. %.

Embodiment 45

A method according to any of embodiments 1-44, wherein ethylene is present in the process gas in an amount of at least 20 mol. %, e.g., in the range of 20 mol. % to 70 mol. %, or 20 mol. % to 60 mol. %, or 20 mol. % to 50 mol. %.

Embodiment 46

A method according to any of embodiments 1-44, wherein ethylene is present in the process gas in an amount of at least 30 mol. %, e.g., in the range of 30 mol. % to 70 mol. %, or 30 mol. % to 60 mol. %, or 30 mol. % to 50 mol. %.

Embodiment 47

A method according to any of embodiments 1-47, wherein acetylene is present in the process gas in an amount of at least 10 ppm, e.g., at least 50 ppm.

Embodiment 48

A method according to any of embodiments 1-47, wherein acetylene is present in the process gas in an amount of at least 100 ppm, e.g., at least 500 ppm.

Embodiment 49

A method according to any of embodiments 1-47, wherein acetylene is present in the process gas in an amount in the range of 10 ppm to 2 mol. %, e.g., 10 ppm to 1 mol. %, or 10 ppm to 0.5 mol %.

Embodiment 50

A method according to any of embodiments 1-47, wherein acetylene is present in the process gas in an amount in the range of 50 ppm to 2 mol. %, e.g., 50 ppm to 1 mol. %, or 50 ppm to 0.5 mol %.

Embodiment 51

A method according to any of embodiments 1-47, wherein acetylene is present in the process gas in an amount in the range of 100 ppm to 2 mol. %, e.g., 100 ppm to 1 mol. %, or 100 ppm to 0.5 mol. %.

Embodiment 52

A method according to any of embodiments 1-47, wherein acetylene is present in the process gas in an amount in the range of 500 ppm to 2 mol. %, or 500 ppm to 1 mol. %, or 500 ppm to 0.5 mol. %.

Embodiment 53

A method according to any of embodiments 1-47, wherein acetylene is present in the process gas in an amount of at least 0.1 mol. %, e.g., at least 0.5 mol % or at least 1 mol. %.

Embodiment 54

A method according to any of embodiments 1-47, wherein acetylene is present in the process gas in an amount in the range of 0.1 mol. % to 2 mol. %, e.g., 0.5 mol. % to 2 mol. %, or 1 mol. % to 2 mol. %, or 0.1 mol. % to 1.5 mol. %, or 0.5 mol. % to 1.5 mol. %, or 1 mol. % to 1.5 mol. %, or 0.1 mol. % to 1 mol. %, or 0.5 mol. % to 1 mol. %.

Embodiment 55

A method according to any of embodiments 1-54, wherein hydrogen is present in the process gas in an amount of at least 6 mol. %, or at least 7 mol. %, or at least 8 mol. %, or at least 9 mol. %, or at least 10 mol. %.

Embodiment 56

A method according to any of embodiments 1-54, wherein hydrogen is present in the process gas in an amount in the range of 5 mol. % to 50 mol. %, e.g., 5 mol. % to 35 mol. %, or 5 mol. % to 20 mol. %, or 5 mol. % to 15 mol. %, or 8 mol. % to 50 mol. %, or 8 mol. % to 35 mol. %, or 8 mol. % to 20 mol. %, or 8 mol. % to 15 mol. %, or 10 mol. % to 50 mol. %, or 10 mol. % to 35 mol. %, or 10 mol. % to 20 mol. %, or 10 mol. % to 15 mol. %.

Embodiment 57

The method according to any of embodiments 1-56, wherein the process gas is provided from an effluent of a cracking process, from an overhead stream of a depropanizer, from an overhead stream of a de-ethanizer, or from a refiner off-gas stream.

Embodiment 58

The method according to any of embodiments 1-57, wherein the process gas contains no more than 10 mol. % (e.g., no more than 5 mol. %, or no more than 2 mol. %, or no more than 1 mol. %) of carbon-containing components other than $C_1$ components (e.g., methane, carbon monoxide, and carbon dioxide), $C_2$ components (e.g., ethylene, ethane, and acetylene) and $C_3$ components (e.g., propane, propylene, propane, methyl acetylene, and propadiene).

Embodiment 59

The method according to any of embodiments 1-57, wherein the process gas contains no more than 20 mol. % (e.g., no more than 15 mol. %, no more than 10 mol. % or no more than 5 mol. %) of carbon-containing components other than ethylene, ethane, acetylene, carbon monoxide, carbon dioxide and methane.

Embodiment 60

A method according to any of embodiments 1-59, wherein the catalyst composition comprises a porous support selected from alumina, silica, titania, and mixtures thereof, present in the catalyst composition in an amount within the range of 90 wt. % to 99.9 wt. %, e.g., 92.5 wt. % to 99.9 wt. %, or 95 wt. % to 99.9 wt. %, or 97.5 wt. % to 99.9 wt. %.

Embodiment 61

A method according to embodiment 60, wherein the porous support is a porous alumina support, e.g., a porous alpha-alumina support.

Embodiment 62

A method according to any of embodiments 1-61, wherein the catalyst composition comprises palladium in an amount of at least 0.02 wt. %, e.g., within the range of 0.02 wt. % to 0.5 wt. %, or 0.03 wt. % to 0.4 wt. %, or 0.04 wt. % to 0.3 wt. %.

Embodiment 63

A method according to any of embodiments 1-62, wherein the catalyst composition comprises the at least one ionic liquid in a total amount up to 10 wt. %.

Embodiment 64

A method according to any of embodiments 1-62, wherein the catalyst composition comprises the at least one ionic liquid in an amount in the range of 0.5 wt. % to 4 wt. %, or 0.5 wt. % to 3 wt. %, or 0.5 wt. % to 2 wt. %.

Embodiment 65

A method according to any of embodiments 1-64, wherein the shell thickness of the ionic liquid at an outer surface of the catalyst is in the range of 10 to 2000 μm, e.g., 100 to 1000 μm, or 100 to 800 μm.

Embodiment 66

A method according to any of embodiments 1-65, wherein the at least one ionic liquid is selected from 1-butyl-3-methylimidazolium triflate, 1-ethyl-3-methylpyridinium ethylsulfate, 1-butyl-1-methylpyrrolidinium triflate, 1-butyl-2,3-dimethylimidazolium triflate, 1-butyl-3-methylimidazolium tricyanomethane, 1-butyl-3-methylimidazolium methylsulfate, 1-butyl-3-methylimidazolium octylsulfate, 1-butyl-3-methylimidazolium tetrafluoroborate, 1-ethyl-3-methylimidazolium ethylsulfate, 1-ethyl-3-methylimidazolium methylphosphonate, 1-ethyl-3-methylimidazolium triflate, 1-butyl-1-methylpyrrolidinium bis(trifluoromethylsulfonyl)imide, 1-butyl-1-methylpyrrolidinium tetracyanoborate, 1-butyl-1-methylpyrrolidinium tris(pentafluoroethyl)trifluorophosphate, 1-butyl-3-methylimidazolium bis(trifluoromethylsulfonyl)imide, 1-butyl-3-methylimidazolium tricyanomethane, 1-ethyl-3-methylpyridinium bis(trifluoromethylsulfonyl)imide, 1-ethyl-3-methylimidazolium tetracyanoborate, 1-ethyl-3-methylimidazolium tris(pentafluoroethyl)trifluorophosphate, 1-methyl-3-octylimidazolium triflate, ethyldimethyl-(2-methoxyethyl)ammonium tris(pentafluoroethyl)trifluorophosphate, tributylmethylammonium dicyanamide, tricyclohexyltetradecylphosphonium tris(pentafluoroethyl)trifluorophosphate, and 1-ethyl-3-methylimidazolium bis(trifluoromethylsulfonyl)imide.

Embodiment 67

A method of starting up a selective hydrogenation reactor, the reactor housing one or more catalyst beds each containing a catalyst suitable for selectively hydrogenating acetylene in a process gas comprising at least 10 mol. % ethylene, at least 1 ppm acetylene, and at least 5 mol. % hydrogen, the method comprising
  providing each catalyst bed at no more than a first temperature, the catalyst of the catalyst bed being in contact with a first gas, the first gas being non-reactive in the presence of the catalyst at the first temperature;
  in the presence of the first gas, heating each catalyst bed to at least a second temperature, the second temperature being at least 20 degrees greater than the first temperature, the first gas being non-reactive in the presence of the catalyst at the second temperature; and then changing the composition of the gas in contact with the catalyst from the first gas to a flow of the process gas while the catalyst bed is at least at the second temperature; and
  allowing the process gas to flow through the catalyst bed until a concentration of acetylene at an outlet of the reactor is less than 1 ppm.

Embodiment 68

The method of embodiment 67, wherein the concentration of acetylene at an outlet of the reactor is less than 1 ppm within six hours (e.g., within four hours or even within two hours) of process gas being introduced to the one or more catalyst beds.

Embodiment 69

The method of embodiment 67 or embodiment 68, wherein the catalyst of each catalyst bed has not been contacted in the reactor with carbon monoxide in an amount in excess of 100 ppm, and wherein the method includes refraining from adding carbon monoxide to the process gas.

Embodiment 70

A method of starting up a selective hydrogenation reactor, the reactor housing one or more catalyst beds each containing a catalyst suitable for selectively hydrogenating acetylene in a process gas comprising at least 10 mol. % ethylene, at least 1 ppm acetylene, and at least 5 mol. % hydrogen, the method comprising
  providing each catalyst bed at no more than a first temperature, the catalyst of the catalyst bed being in contact with the process gas;
  in the presence of the process gas, heating each catalyst bed to at least a second temperature, the second temperature being at least 20 degrees greater than the first temperature, the heating of each catalyst bed being performed at a rate in the range of at least 3° C./hour; and
  allowing the process gas to flow through the catalyst bed until a concentration of acetylene at an outlet of the reactor is less than 1 ppm.

Embodiment 71

The method of embodiment 70, wherein the rate is in the range of 3-20° C./hour, e.g., 3-15° C./hour or 3-12° C./hour.

Embodiment 72

The method of embodiment 70, wherein the rate is in the range of 6-20° C./hour, e.g., 6-15° C./hour or 6-12° C./hour.

Embodiment 73

The method of embodiment 70, wherein the rate is in the range of 9-20° C./hour, e.g., 9-15° C./hour.

Embodiment 74

A method of starting up a selective hydrogenation reactor, the reactor housing one or more catalyst beds each containing a catalyst suitable for selectively hydrogenating acetylene in a process gas comprising at least 10 mol. % ethylene, at least 1 ppm acetylene, and at least 5 mol. % hydrogen, the method comprising;
   providing the reactor with each catalyst bed having its catalyst in contact with a first gas, the first gas being non-reactive in the presence of the catalyst at the first temperature, wherein the catalyst has not been contacted in the reactor with a carbon monoxide-containing gas having a carbon monoxide concentration in excess of 2000 ppm; and
   introducing a flow of the process gas to the one or more catalyst beds, and refraining from adding carbon monoxide to the process gas.

Embodiment 75

The method of embodiment 74, further comprising raising the catalyst bed temperature of each catalyst bed from no more than a first temperature to at least a second temperature.

Embodiment 76

The method of embodiment 75, wherein the catalyst bed temperature(s) are raised before the process gas is introduced.

Embodiment 77

The method of claim 75, wherein the catalyst bed temperature(s) are raised after the process gas is introduced.

Embodiment 78

The method of claim 75, wherein the process gas is introduced while the catalyst bed temperature(s) are raised.

Embodiment 79

The method of any of embodiments 75-78, further comprising, after raising the temperature to at least the second temperature, flowing process gas through the one or more catalyst beds until a reactor effluent has less than 1 ppm (e.g., less than 0.5 ppm) acetylene.

Embodiment 80

The method according to any of embodiments 67-79, wherein the first temperature is no more than 50° C., e.g., in the range of 31-50° C. or 35-50° C., or 40-50° C., or 45-50° C.

Embodiment 81

The method according to any of embodiments 67-79, wherein the first temperature is no more than 45° C., e.g., in the range of 31-45° C. or 35-45° C., or 40-45° C.

Embodiment 82

The method according to any of embodiments 67-79, wherein the first temperature is no more than 40° C., e.g., in the range of 31-40° C. or 35-40° C.

Embodiment 83

The method according to any of embodiments 67-79, wherein the first temperature is no more than 30° C., or no more than 25° C.

Embodiment 84

A method of starting up a selective hydrogenation reactor, the reactor housing one or more catalyst beds each containing a catalyst suitable for selectively hydrogenating acetylene in a process gas comprising at least 10 mol. % ethylene, at least 1 ppm acetylene, and at least 5 mol. % hydrogen, the method comprising
   drying the one or more catalyst beds at a temperature of at least 50° C.; then cooling each dried catalyst bed to a first temperature in the range of 31-50° C., and contacting the catalyst of each catalyst with the process gas at the first temperature; then
   in the presence of the process gas, heating each catalyst bed to at least a second temperature, the second temperature being at least 20 degrees greater than the first temperature; and
   allowing the process gas to flow through the catalyst bed until a concentration of acetylene at an outlet of the reactor is less than 1 ppm.

Embodiment 85

A method according to embodiment 84, wherein the first temperature is within the range of 35° C. to 50° C., e.g., 40° C. to 50° C., or 45° C. to 50° C.

Embodiment 86

A method according to embodiment 84, wherein the first temperature is within the range of 31° C. to 45° C., e.g., 35° C. to 45° C., or 40° C. to 45° C.

Embodiment 87

A method according to embodiment 84, wherein the first temperature is within the range of 31° C. to 40° C., e.g., 35° C. to 40° C.

Embodiment 88

A method according to any of embodiments 67-87, wherein the second temperature is within the range of 40° C. to 140° C.

Embodiment 89

A method according to any of embodiments 67-87, wherein the second temperature is within the range of 40° C. to 100° C.

Embodiment 90

A method according to any of embodiments 67-87, wherein the second temperature is within the range of 40° C. to 90° C.

Embodiment 91

A method according to any of embodiments 67-87, wherein the second temperature is within the range of 50° C. to 90° C.

Embodiment 92

A method according to any of embodiments v, wherein the second temperature is within the range of 50° C. to 100° C.

Embodiment 93

A method according to any of embodiments 67-87, wherein the second temperature is within the range of 20° C. to 130° C., e.g., in the range of 20° C. to 120° C., or 20° C. to 110° C., or 20° C. to 100° C., or 20° C. to 90° C.

Embodiment 94

A method according to any of embodiments 67-87, wherein the second temperature is within the range of 40° C. to 140° C., e.g., 40° C. to 130° C., or 40° C. to 120° C., or 40° C. to 110° C.

Embodiment 95

A method according to any of embodiments 67-87, wherein the second temperature is within the range of 50° C. to 140° C., e.g., 50° C. to 130° C., or 50° C. to 120° C., or 50° C. to 110° C.

Embodiment 96

A method according to any of embodiments 67-87, wherein the second temperature is within the range of 60° C. to 140° C., e.g., 60° C. to 130° C., or 60° C. to 120° C., or 60° C. to 110° C., or 60° C. to 100° C., or 60° C. to 90° C.

Embodiment 97

A method according to any of embodiments 67-96, wherein the second temperature is at least 30° C. greater (e.g., at least 40° C. greater) than the first temperature.

Embodiment 98

A method according to any of embodiments 67-96, wherein the second temperature is at least 50° C. greater (e.g., at least 60° C. greater) than the first temperature.

Embodiment 99

The method according to any of embodiments 67-98, wherein the temperature of each catalyst bed is raised from no more than the first temperature to at least the second temperature over a time period of no more than 10 hours, e.g., no more than six hours.

Embodiment 100

A method according to any of embodiments 67-69, 74-83 and 88-99, wherein the first gas includes no more than 1 ppm acetylene (e.g., no more than 0.5 ppm).

Embodiment 101

A method according to any of embodiments 67-100, wherein the process gas includes at least 10 ppm CO.

Embodiment 102

A method according to any of embodiments 67-100, wherein the process gas is otherwise as described with respect to one or more of embodiments 1-66.

Embodiment 103

A method according to any of embodiments 67-69, 74-83 and 88-102, wherein each catalyst bed is changed from contacting the first gas to contacting the process gas over a time period of no more than 10 hours, e.g., no more than six hours, e.g., in the range of 2-10 hours, 4-10 hours, or 3-6 hours.

Embodiment 104

The method according to any of embodiments 67-104, wherein the catalyst is as described in one or more of embodiments 1-66 Embodiment 105. A method according to any of embodiments 1-104, further comprising, before introducing the process gas to the bed or contacting the catalyst composition with the process gas, reducing the catalyst (e.g., with a flow of a hydrogen-containing gas).

Embodiment 106

A hydrogenation catalyst composition comprising:
a porous support, present in the composition in an amount within the range of 90 wt. % to 99.9 wt. %;
palladium, present in the composition in an amount within the range of 0.02 wt. % to 0.5 wt. % (e.g., within the range of 0.03 wt. % to 0.4 wt. %, or 0.04 wt. % to 0.3 wt. %), calculated on an elemental mass basis; and
one or more ionic liquids, present in the composition in a combined amount up to 10 wt. %.

Embodiment 107

The catalyst composition of embodiment 106, wherein palladium is present in the composition in an amount within the range of 0.02 wt. % to 0.5 wt. %, for example, 0.02 wt. % to 0.4 wt. %, or 0.02 wt. % to 0.3 wt. %, or 0.02 wt. % to 0.2 wt. %, or 0.02 wt. % to 0.15 wt. %.

Embodiment 108

The catalyst composition of embodiment 106, wherein palladium is present in the composition in an amount within the range of 0.04 wt. % to 0.5 wt. %, for example, 0.04 wt. % to 0.4 wt. %, or 0.04 wt. % to 0.3 wt. %, or 0.04 wt. % to 0.2 wt. %, or 0.04 wt. % to 0.15 wt. %.

Embodiment 109

The catalyst composition of embodiment 106, wherein palladium is present in the composition in an amount within the range of 0.05 wt. % to 0.5 wt. %, for example, 0.05 wt. % to 0.4 wt. %, or 0.05 wt. % to 0.3 wt. %, or 0.05 wt. % to 0.2 wt. %, or 0.05 wt. % to 0.15 wt. %.

Embodiment 110

The catalyst composition of embodiment 106, wherein palladium is present in the composition in an amount within the range of 0.06 wt. % to 0.5 wt. %, for example, 0.06 wt. % to 0.4 wt, or 0.06 wt. % to 0.3 wt, or 0.06 wt. % to 0.2 wt. %, or 0.06 wt. % to 0.15 wt. %.

Embodiment 111

The catalyst composition of embodiment 106, wherein palladium is present in the composition in an amount within the range of 0.08 wt. % to 0.5 wt. %, for example, 0.08 wt. % to 0.4 wt. %, or 0.08 wt. % to 0.3 wt. %, or 0.07 wt. % to 0.2 wt. %, or 0.07 wt. % to 0.15 wt. %.

Embodiment 112

A hydrogenation catalyst composition comprising:
a porous support, present in the composition in an amount within the range of 90 wt. % to 99.9 wt. %, having a BET surface area of no more than 10 $m^2/g$ and a pore volume of at least 0.1 mL/g;
palladium, present in the composition in an amount within the range of at least 0.02 wt. %, calculated on an elemental mass basis; and
one or more ionic liquids, present in the composition in a combined amount up to 10 wt. %.

Embodiment 113

The hydrogenation catalyst of embodiment 112, comprising palladium in an amount of at least 0.03 wt. %, or at least 0.04 wt. %, or at least 0.05 wt. %, or at least 0.06 wt. %, or at least 0.07 wt. %, or at least 0.08 wt. %, or at least 0.09 wt. %, or at least 0.1 wt. %, or at least 0.11 wt. %, or at least 0.12 wt. %, or at least 0.13 wt. %, or at least 0.14 wt. %, or at least 0.15 wt. %.

Embodiment 114

The hydrogenation catalyst of embodiment 112, comprising palladium in an amount of no more than 0.5 wt. % (e.g., no more than 0.4 wt. %, or no more than 0.3 wt. %, or no more than 0.2 wt. %).

Embodiment 115

The hydrogenation catalyst of embodiment 112, comprising palladium in an amount within the range of 0.02 wt. % to 0.5 wt. %, or 0.02 wt. % to 0.45 wt. %, or 0.03 wt. % to 0.4 wt. %, or 0.03 wt. % to 0.35 wt. %, or 0.04 wt. % to 0.3 wt. %, or 0.04 wt. % to 0.25 wt. %.

Embodiment 116

The catalyst composition of any of embodiments 106-115, further comprising at least one promoter (e.g., silver, gold, zinc, tin, lead, gallium, cadmium, copper, bismuth, sodium, cesium, or potassium), present in the composition in an amount within the range of 0.05 wt. % to 0.25 wt. %, e.g., 0.08 wt. % to 0.25 wt. %, or 0.1 wt. % to 0.25 wt. %, calculated on an elemental mass basis.

Embodiment 117

The hydrogenation catalyst of any of embodiments 106-116, wherein the porous support has a BET surface area within the range of 2 $m^2/g$ to 10 $m^2/g$.

Embodiment 118

The hydrogenation catalyst of any of embodiments 106-116, the porous support has a BET surface area within the range of 2 $m^2/g$ to 9 $m^2/g$, or 2 $m^2/g$ to 8 $m^2/g$, or 2 $m^2/g$ to 7 $m^2/g$, or 2 $m^2/g$ to 6 $m^2/g$, or 2 $m^2/g$ to 5 $m^2/g$, or 3 $m^2/g$ to 10 $m^2/g$, or 4 $m^2/g$ to 10 $m^2/g$, or 5 $m^2/g$ to 10 $m^2/g$, or 6 $m^2/g$ to 10 $m^2/g$, or 2 $m^2/g$ to 6 $m^2/g$, or 3 $m^2/g$ to 7 $m^2/g$, or 4 $m^2/g$ to 8 $m^2/g$, or 5 $m^2/g$ to 9 $m^2/g$.

Embodiment 119

The hydrogenation catalyst of any of embodiments 106-118, wherein the porous support has a pore volume within the range of 0.10 mL/g to 1.0 mL/g.

Embodiment 120

The hydrogenation catalyst of any of 106-118, wherein the porous support has a pore volume within the range of 0.10 mL/g to 0.80 mL/g, or 0.20 mL/g to 0.80 mL/g, or 0.30 mL/g to 0.80 mL/g, or 0.20 mL/g to 0.70 mL/g, or 0.30 mL/g to 0.70 mL/g.

Embodiment 121

A hydrogenation catalyst composition comprising:
a porous support, present in the composition in an amount within the range of 90 wt. % to 99.9 wt. %;
palladium, present in the composition in an amount within the range of at least 0.02 wt. %, calculated on an elemental mass basis; and
one or more ionic liquids, present in the composition in a combined amount up to 10 wt. %,
wherein the hydrogenation catalyst has a BET surface area of no more than 10 $m^2/g$ and a pore volume of at least 0.05 mL/g.

Embodiment 122

The hydrogenation catalyst of embodiment 121, comprising palladium in an amount of at least 0.03 wt. %, or at least 0.04 wt. %, or at least 0.05 wt. %, or at least 0.06 wt. %, or at least 0.07 wt. %, or at least 0.08 wt. %, or at least 0.09 wt. %, or at least 0.1 wt. %, or at least 0.11 wt. %, or at least 0.12 wt. %, or at least 0.13 wt. %, or at least 0.14 wt. %, or at least 0.15 wt. %.

Embodiment 123

The hydrogenation catalyst of embodiment 121 or embodiment 122, comprising palladium in an amount of no more than 0.5 wt. % (e.g., no more than 0.4 wt. %, or no more than 0.3 wt. %, or no more than 0.2 wt. %).

Embodiment 124

The hydrogenation catalyst of embodiment 121, comprising palladium in an amount within the range of 0.02 wt. % to 0.5 wt. %, or 0.02 wt. % to 0.45 wt. %, or 0.03 wt. % to 0.4 wt. %, or 0.03 wt. % to 0.35 wt. %, or 0.04 wt. % to 0.3 wt. %, or 0.04 wt. % to 0.25 wt. %.

Embodiment 125

The hydrogenation catalyst of any of embodiments 121-124, further comprising at least one promoter (e.g., silver, gold, zinc, tin, lead, gallium, cadmium, copper, bismuth, sodium, cesium, or potassium), present in the composition in an amount within the range of 0.05 wt. % to 0.25 wt. %, e.g., 0.08 wt. % to 0.25 wt. %, or 0.1 wt. % to 0.25 wt. %, calculated on an elemental mass basis.

Embodiment 126

The hydrogenation catalyst of any of embodiments 121-125, having a BET surface area within the range of 2 $m^2/g$ to 10 $m^2/g$.

Embodiment 127

The hydrogenation catalyst of any of embodiments 121-125, having a BET surface area within the range of 2 $m^2/g$ to 9 $m^2/g$, or 2 $m^2/g$ to 8 $m^2/g$, or 2 $m^2/g$ to 7 $m^2/g$, or 2 $m^2/g$ to 6 $m^2/g$, or 2 $m^2/g$ to 5 $m^2/g$, or 3 $m^2/g$ to 10 $m^2/g$, or 4 $m^2/g$ to 10 $m^2/g$, or 5 $m^2/g$ to 10 $m^2/g$, or 6 $m^2/g$ to 10 $m^2/g$, or 2 $m^2/g$ to 6 $m^2/g$, or 3 $m^2/g$ to 7 $m^2/g$, or 4 $m^2/g$ to 8 $m^2/g$, or 5 $m^2/g$ to 9 $m^2/g$.

Embodiment 128

The hydrogenation catalyst of any of embodiments 121-127, having a pore volume within the range of 0.05 mL/g to 1.0 mL/g.

Embodiment 129

The hydrogenation catalyst of any of embodiments 121-127, having a pore volume within the range of 0.05 mL/g to 0.4 mL/g.

Embodiment 130

The hydrogenation catalyst of any of embodiments 121-129, having a pore volume within the range of 0.10 mL/g to 1.0 mL/g, e.g., 0.10 mL/g to 0.80 mL/g, or 0.10 to 0.60 mL/g, or 0.10 to 0.40 mL/g, or 0.10 to 0.30 mL/g.

Embodiment 131

The hydrogenation catalyst of any of embodiments 121-129, having a pore volume within the range of 0.20 mL/g to 1.0 mL/g, e.g., 0.20 mL/g to 0.80 mL/g, or 0.20 to 0.60 mL/g, or 0.20 to 0.40 mL/g, or 0.20 to 0.35 mL/g.

Embodiment 132

The hydrogenation catalyst of any of embodiments 121-129, having a pore volume within the range of 0.40 mL/g to 1.0 mL/g, e.g., 0.40 mL/g to 0.80 mL/g, or 0.40 to 0.60 mL/g.

Embodiment 133

They hydrogenation catalyst of any of embodiments 121-132, wherein the difference between the pore volume of the support and the pore volume of the catalyst (i.e., including the palladium, any promoters and the ionic liquid) is in the range of 10-90% of the pore volume of the support.

Embodiment 134

They hydrogenation catalyst of any of embodiments 121-132, wherein the difference between the pore volume of the support and the pore volume of the catalyst (i.e., including the palladium, any promoters and the ionic liquid) is in the range of 10-80% of the pore volume of the support, e.g., 20-80%, or 30-80%, or 40-80% of the pore volume of the support.

Embodiment 135

They hydrogenation catalyst of any of embodiments 121-132, wherein the difference between the pore volume of the support and the pore volume of the catalyst (i.e., including the palladium, any promoters and the ionic liquid) is in the range of 10-70% of the pore volume of the support, e.g., 20-70%, or 30-70%, or 40-70%; or in the range of 10-60% of the pore volume of the support, e.g., 20-60%, or 30-60%, or 40-60%.

Embodiment 136

The hydrogenation catalyst of any of claims 106-135, wherein the ionic liquid is present in an amount in the range of 0.1 wt. % to 10 wt. %, e.g., 0.1 wt. % to 8 wt. %, or 0.1 wt. % to 6 wt. %, or 0.1 wt. % to 4 wt. %, or 0.1 wt. % to 3 wt. %, or 0.1 wt. % to 2 wt. %, or 0.1 wt. % to 1 wt. %.

Embodiment 137

The hydrogenation catalyst of any of embodiments 106-135, wherein the ionic liquid is present in an amount in the range of 0.2 to 3 wt. %.

Embodiment 138

The hydrogenation catalyst of any of embodiments 106-135, wherein the ionic liquid is present in an amount in the range of 0.5 to 4 wt. %.

Embodiment 139

The hydrogenation catalyst of any of embodiments 106-138, having silver as a promoter.

Embodiment 140

The hydrogenation catalyst of any of embodiments 106-139, wherein the porous support is a porous alumina support, e.g., a porous alpha alumina support.

Embodiment 141

The hydrogenation catalyst of any of embodiments 106-140, wherein the shell thickness of the ionic liquid at an outer surface of the catalyst is in the range of 10 to 2000 μm, e.g., 100 to 1000 μm, or 100 to 800 μm.

Embodiment 142

The hydrogenation catalyst of any of embodiments 106-138, wherein the at least one ionic liquid is selected from 1-butyl-3-methylimidazolium triflate, 1-ethyl-3-methylpyridinium ethylsulfate, 1-butyl-1-methylpyrrolidinium triflate, 1-butyl-2,3-dimethylimidazolium triflate, 1-butyl-3-methylimidazolium tricyanomethane, 1-butyl-3-methylimidazolium methylsulfate, 1-butyl-3-methylimidazolium octylsulfate, 1-butyl-3-methylimidazolium tetrafluoroborate, 1-ethyl-3-methylimidazolium ethylsulfate, 1-ethyl-3-methylimidazolium methylphosphonate, 1-ethyl-3-methylimidazolium triflate, 1-butyl-1-methylpyrrolidinium bis(trifluoromethylsulfonyl)imide, 1-butyl-1-methylpyrrolidinium tetracyanoborate, 1-butyl-1-methylpyrrolidinium tris(pentafluoroethyl)trifluorophosphate, 1-butyl-3-methylimidazolium bis(trifluoromethylsulfonyl)imide, 1-butyl-3-methylimidazolium tricyanomethane, 1-ethyl-3-methylpyridinium bis(trifluoromethylsulfonyl)imide, 1-ethyl-3-methylimidazolium tetracyanoborate, 1-ethyl-3-methylimidazolium tris(pentafluoroethyl)trifluorophosphate, 1-methyl-3-octylimidazolium triflate, ethyldimethyl-(2-methoxyethyl)ammonium tris(pentafluoroethyl)trifluorophosphate, tributylmethylammonium dicyanamide, tricyclohexyltetradecylphosphonium tris(pentafluoroethyl)trifluorophosphate, and 1-ethyl-3-methylimidazolium bis(trifluoromethylsulfonyl)imide.

Embodiment 143

Any of the processes of embodiments 1-59 and 67-105, using the catalyst as described in any of embodiments 106-142.

What is claimed is:

1. A method for selectively hydrogenating acetylene, the method comprising contacting a catalyst composition with a process gas comprising
   ethylene, present in the process gas in an amount of at least 10 mol. %;
   acetylene, present in the process gas in an amount of at least about 1 ppm, calculated on a molar basis;
   hydrogen, present in the process gas in amount of at least 5 mol. %; and
   0 ppm to 120 ppm carbon monoxide, calculated on a molar basis;
   wherein the catalyst composition comprises
   a porous support, present in the catalyst composition in an amount within a range of 90 wt. % to 99.9 wt. %;
   palladium, present in the catalyst composition in an amount within a range of at least 0.02 wt. %, calculated on an elemental mass basis; and
   one or more ionic liquids, present in the catalyst composition in a combined amount in a range of 0.1 wt. % to 10 wt. %;
   wherein the process gas is contacted with the catalyst composition at a gas hourly space velocity (GHSV) based on a total catalyst volume in one bed or multiple beds in a range of 7,500 $h^{-1}$ to 30,000 $h^{-1}$; and
   wherein at least 90% of the acetylene present in the process gas is hydrogenated, and no more than 1 mol. % of the total of acetylene and ethylene present in the process gas is converted to ethane.

2. A method according to claim 1, wherein the gas hourly space velocity is in a range of 10,000 $h^{-1}$ to 30,000 $h^{-1}$.

3. A method according to claim 1, wherein the contacting is conducted at a temperature within a range of 20° C. to 140° C.

4. A method according to claim 1, wherein the contacting is conducted at a temperature within a range of 40° C. to 100° C.

5. A method according to claim 1, wherein carbon monoxide is present in the process gas in an amount in a range of 0 ppm to 90 ppm, calculated on a molar basis.

6. A method according to claim 1, wherein at least 95% of the acetylene present in the process gas is hydrogenated.

7. A method according to claim 1, wherein an amount of ethane in the product of the selective hydrogenation is no more than 0.5 mol. % greater than the amount of ethane in the process gas.

8. A method according to claim 1, wherein ethylene is present in the process gas in an amount of at least 20 mol. %.

9. A method according to claim 1, wherein acetylene is present in the process gas in an amount of at least 500 ppm, calculated on a molar basis.

10. A method according to claim 1, wherein hydrogen is present in the process gas in an amount in a range of 5 mol. % to 35 mol. %.

11. The method according to claim 1, wherein the process gas contains no more than 5 mol. % of carbon-containing components other than $C_1$ components, $C_2$ components and $C_3$ components.

12. A method according to claim 1, wherein the catalyst composition comprises a porous support selected from alumina, silica, titania, and mixtures thereof, present in the catalyst composition in an amount within a range of 90 wt. % to 99.9 wt. %.

13. A method according to claim 1, wherein the catalyst composition comprises palladium in an amount of at least 0.05 wt. %.

14. A method according to claim 1, wherein the catalyst composition comprises the at least one ionic liquid in a total amount in a range of 0.1 wt. % to 2 wt. %.

15. A method according to claim 1, wherein the at least one ionic liquid is selected from 1-butyl-3-methylimidazolium triflate, 1-ethyl-3-methylpyridinium ethylsulfate, 1-butyl-1-methylpyrrolidinium triflate, 1-butyl-2,3-dimethylimidazolium triflate, 1-butyl-3-methylimidazolium tricyanomethane, 1-butyl-3-methylimidazolium methylsulfate, 1-butyl-3-methylimidazolium octylsulfate, 1-butyl-3-methylimidazolium tetrafluoroborate, 1-ethyl-3-methylimidazolium ethylsulfate, 1-ethyl-3-methylimidazolium methylphosphonate, 1-ethyl-3-methylimidazolium triflate, 1-butyl-1-methylpyrrolidinium bis(trifluoromethylsulfonyl)imide, 1-butyl-1-methylpyrrolidinium tetracyanoborate, 1-butyl-1-methylpyrrolidinium tris(pentafluoroethyl)trifluorophosphate, 1-butyl-3-methylimidazolium bis(trifluoromethylsulfonyl)imide, 1-butyl-3-methylimidazolium tricyanomethane, 1-ethyl-3-methylpyridinium bis(trifluoromethylsulfonyl)imide, 1-ethyl-3-methylimidazolium tetracyanoborate, 1-ethyl-3-methylimidazolium tris(pentafluoroethyl)trifluorophosphate, 1-methyl-3-octylimidazolium triflate, ethyldimethyl-(2-methoxyethyl)ammonium tris(pentafluoroethyl)trifluorophosphate, tributylmethylammonium dicyanamide, tricyclohexyltetradecylphosphonium tris(pentafluoroethyl)trifluorophosphate, and 1-ethyl-3-methylimidazolium bis(trifluoromethylsulfonyl)imide.

16. The method according to claim 1, wherein the catalyst composition comprises:
   a porous support, present in the catalyst composition in an amount within a range of 90 wt. % to 99.9 wt. %;
   palladium, present in the catalyst composition in an amount within a range of 0.02 wt. % to 0.5 wt. %, calculated on an elemental mass basis; and
   one or more ionic liquids, present in the catalyst composition in a combined amount in a range of 0.1 wt. % to 2 wt. %.

17. The method according to claim 1, wherein the catalyst composition has a BET surface area of no more than 10 $m^2/g$ and a pore volume of at least 0.05 mL/g.

18. A method according to claim 1, wherein carbon monoxide is present in the process gas in an amount in a range of 50 to 100 ppm, calculated on a molar basis.

19. A method according to claim 1, wherein carbon monoxide is present in the process gas in an amount in a range of 25 wt. % to 80 ppm, calculated on a molar basis.

20. A method according to claim 1, wherein carbon monoxide is present in the process gas in an amount in a range of 25-90 ppm, calculated on a molar basis.

21. A method according to claim 1, wherein
the contacting is conducted at a temperature within a range of 20° C. to 140° C.;
carbon monoxide is present in the process gas in an amount of 25-90 ppm, calculated on a molar basis;
at least 95% of the acetylene present in the process gas is hydrogenated;
an amount of ethane in the product of the selective hydrogenation is no more than 0.5 mol. % greater than the amount of ethane in the process gas;
ethylene is present in the process gas in an amount of at least 20 mol. %;
acetylene is present in the process gas in an amount of at least 500 ppm, calculated on a molar basis;
hydrogen is present in the process gas in an amount in a range of 5 mol. % to 35 mol. %;
the process gas contains no more than 5 mol. % of carbon-containing components other than $C_1$ components, $C_2$ components and $C_3$ components;
the catalyst composition comprises a porous support selected from alumina, silica, titania, and mixtures thereof, present in the catalyst composition in an amount within a range of 90 wt. % to 99.9 wt. %, palladium in an amount of at least 0.05 wt. %, the at least one ionic liquid in a total amount in a range of 0.1 wt. % to 2 wt. %.

22. The method according to claim 1, wherein the method for selectively hydrogenating acetylene is configured as a front-end hydrogenation.

* * * * *